United States Patent
Scharf et al.

(10) Patent No.: US 10,314,497 B2
(45) Date of Patent: *Jun. 11, 2019

(54) DEVICE AND METHOD FOR THE GEOMETRIC DETERMINATION OF ELECTRICAL DIPOLE DENSITIES ON THE CARDIAC WALL

(71) Applicant: Acutus Medical, Inc., Carlsbad, CA (US)

(72) Inventors: Christoph Scharf, Horgen (CH); Gunter Scharf, Dubendorf (CH); Randell L. Werneth, Boise, ID (US)

(73) Assignee: ACUTUS MEDICAL INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/926,187

(22) Filed: Mar. 20, 2018

(65) Prior Publication Data

US 2018/0271381 A1    Sep. 27, 2018

Related U.S. Application Data

(63) Continuation of application No. 15/672,020, filed on Aug. 8, 2017, now Pat. No. 9,968,268, which is a (Continued)

(51) Int. Cl.
*A61B 5/00*    (2006.01)
*A61B 5/04*    (2006.01)
(Continued)

(52) U.S. Cl.
CPC ........ *A61B 5/0205* (2013.01); *A61B 5/04012* (2013.01); *A61B 5/0422* (2013.01);
(Continued)

(58) Field of Classification Search
CPC . A61B 5/0205; A61B 5/04012; A61B 5/0422; A61B 5/4836; A61B 5/6858;
(Continued)

(56) References Cited

U.S. PATENT DOCUMENTS

| 5,041,973 A | 8/1991 | Lebron et al. |
| 5,156,151 A | 10/1992 | Imran |

(Continued)

FOREIGN PATENT DOCUMENTS

| CA | 2829626 | 9/2012 |
| CN | 201223445 | 4/2009 |

(Continued)

OTHER PUBLICATIONS

European Office Action dated Apr. 23, 2018 issued in corresponding European Application No. 07785075.8.

(Continued)

*Primary Examiner* — John R Downey
(74) *Attorney, Agent, or Firm* — Onello & Mello, LLP

(57) ABSTRACT

Disclosed are devices, systems, and methods for determining the dipole densities on heart walls. In particular, a triangularization of the heart wall is performed in which the dipole density of each of multiple regions correlate to the potential measured at various located within the associated chamber of the heart. To create a database of dipole densities, mapping information recorded by multiple electrodes located on one or more catheters and anatomical information is used. In addition, skin electrodes may be implemented. Additionally, one or more ultrasound elements are provided, such as on a clamp assembly or integral to a mapping electrode, to produce real time images of device components and surrounding structures.

31 Claims, 5 Drawing Sheets

Related U.S. Application Data continuation of application No. 14/003,671, filed as application No. PCT/US2012/028593 on Mar. 9, 2012, now Pat. No. 9,757,044.

(60) Provisional application No. 61/451,357, filed on Mar. 10, 2011.

(51) Int. Cl.
| | |
|---|---|
| *A61B 5/06* | (2006.01) |
| *A61B 8/00* | (2006.01) |
| *A61B 8/08* | (2006.01) |
| *A61B 8/12* | (2006.01) |
| *A61B 18/14* | (2006.01) |
| *A61B 5/042* | (2006.01) |
| *A61B 5/0205* | (2006.01) |

(52) U.S. Cl.
CPC .......... *A61B 5/4836* (2013.01); *A61B 5/6858* (2013.01); *A61B 8/0841* (2013.01); *A61B 8/0883* (2013.01); *A61B 8/12* (2013.01); *A61B 8/445* (2013.01); *A61B 8/4483* (2013.01); *A61B 8/5207* (2013.01); *A61B 18/1492* (2013.01); *A61B 5/065* (2013.01); *A61B 5/6869* (2013.01); *A61B 2562/0204* (2013.01); *A61B 2562/0209* (2013.01); *A61B 2576/023* (2013.01)

(58) Field of Classification Search
CPC ....... A61B 8/0841; A61B 8/0883; A61B 8/12; A61B 8/445; A61B 8/4483; A61B 8/5207; A61B 18/1492
See application file for complete search history.

(56) References Cited

U.S. PATENT DOCUMENTS

| | | | |
|---|---|---|---|
| 5,293,868 A | 3/1994 | Nardella | |
| 5,482,472 A | 1/1996 | Garoni et al. | |
| 5,499,981 A | 3/1996 | Kordis | |
| 5,555,883 A | 9/1996 | Avitall | |
| 5,595,183 A | 1/1997 | Swanson et al. | |
| 5,601,084 A | 2/1997 | Sheehan et al. | |
| 5,647,367 A * | 7/1997 | Lum | A61B 8/12 600/463 |
| 5,662,108 A | 9/1997 | Budd et al. | |
| 5,722,402 A | 3/1998 | Swanson et al. | |
| 5,722,416 A | 3/1998 | Swanson et al. | |
| 5,740,808 A * | 4/1998 | Panescu | A61B 5/0066 600/424 |
| 5,749,833 A * | 5/1998 | Hakki | A61B 5/042 600/380 |
| 5,759,158 A | 6/1998 | Swanson | |
| 5,795,298 A * | 8/1998 | Vesely | A61B 5/0422 600/374 |
| 5,795,299 A | 8/1998 | Eaton et al. | |
| 5,820,568 A | 10/1998 | Willis | |
| 5,876,336 A | 3/1999 | Swanson et al. | |
| 5,928,228 A | 7/1999 | Kordis et al. | |
| 5,968,040 A | 10/1999 | Swanson et al. | |
| 6,014,590 A | 1/2000 | Whayne et al. | |
| 6,024,703 A | 2/2000 | Zanelli et al. | |
| 6,066,096 A | 5/2000 | Smith et al. | |
| 6,086,532 A | 7/2000 | Panescu et al. | |
| 6,107,699 A | 8/2000 | Swanson | |
| 6,187,032 B1 | 2/2001 | Ohyu et al. | |
| 6,188,928 B1 | 2/2001 | Noren et al. | |
| 6,216,027 B1 | 4/2001 | Willis et al. | |
| 6,216,043 B1 | 4/2001 | Swanson et al. | |
| 6,240,307 B1 | 5/2001 | Beatty et al. | |
| 6,301,496 B1 | 10/2001 | Reisfeld | |
| 6,400,981 B1 | 6/2002 | Govari | |
| 6,490,474 B1 | 12/2002 | Willis et al. | |
| 6,514,249 B1 * | 2/2003 | Maguire | A61B 18/00 606/37 |
| 6,574,492 B1 | 6/2003 | Ben-Haim et al. | |
| 6,640,119 B1 | 10/2003 | Budd et al. | |
| 6,716,166 B2 | 4/2004 | Govari | |
| 6,728,562 B1 | 4/2004 | Budd et al. | |
| 6,772,004 B2 | 8/2004 | Rudy | |
| 6,773,402 B2 | 8/2004 | Govari et al. | |
| 6,824,515 B2 * | 11/2004 | Suorsa | A61B 18/1492 600/439 |
| 6,826,420 B1 | 11/2004 | Beatty et al. | |
| 6,826,421 B1 | 11/2004 | Beatty et al. | |
| 6,839,588 B1 | 1/2005 | Rudy | |
| 6,895,267 B2 | 5/2005 | Panescu et al. | |
| 6,939,309 B1 | 9/2005 | Beatty et al. | |
| 6,950,689 B1 | 9/2005 | Willis et al. | |
| 6,970,733 B2 | 11/2005 | Willis et al. | |
| 6,978,168 B2 | 12/2005 | Beatty et al. | |
| 6,990,370 B1 | 1/2006 | Beatty et al. | |
| 7,187,964 B2 | 3/2007 | Khoury | |
| 7,258,674 B2 | 8/2007 | Hillstead et al. | |
| 7,263,397 B2 | 8/2007 | Hauck et al. | |
| 7,285,119 B2 | 10/2007 | Stewart et al. | |
| 7,289,843 B2 | 10/2007 | Beatty et al. | |
| 7,291,146 B2 | 11/2007 | Steinke et al. | |
| 7,479,141 B2 | 1/2009 | Kleen et al. | |
| 7,505,810 B2 | 3/2009 | Harlev et al. | |
| 7,573,182 B2 | 8/2009 | Savage | |
| 7,689,261 B2 | 3/2010 | Mohr et al. | |
| 7,766,838 B2 | 8/2010 | Yagi et al. | |
| 7,841,986 B2 | 11/2010 | He et al. | |
| 7,918,793 B2 | 4/2011 | Altmann et al. | |
| 7,953,475 B2 | 5/2011 | Harlev et al. | |
| 8,103,327 B2 | 1/2012 | Harlev et al. | |
| 8,147,486 B2 | 4/2012 | Honour et al. | |
| 8,150,499 B2 | 4/2012 | Gelbart et al. | |
| 8,208,998 B2 | 6/2012 | Beatty et al. | |
| 8,233,972 B2 | 7/2012 | Zhang | |
| 8,346,339 B2 | 1/2013 | Kordis et al. | |
| 8,360,786 B2 | 1/2013 | Duryea | |
| 8,364,234 B2 | 1/2013 | Kordis et al. | |
| 8,412,307 B2 | 4/2013 | Willis et al. | |
| 8,417,313 B2 | 4/2013 | Scharf et al. | |
| 8,428,690 B2 | 4/2013 | Li et al. | |
| 8,447,377 B2 | 5/2013 | Harlev et al. | |
| 8,454,596 B2 | 6/2013 | Ma et al. | |
| 8,465,433 B2 | 6/2013 | Zwirn | |
| 8,478,388 B2 | 7/2013 | Nguyen et al. | |
| 8,512,255 B2 | 8/2013 | Scharf et al. | |
| 8,571,647 B2 | 10/2013 | Harlev et al. | |
| 8,700,119 B2 | 4/2014 | Scharf et al. | |
| 8,755,861 B2 | 6/2014 | Harlev et al. | |
| 8,825,130 B2 | 9/2014 | Just et al. | |
| 8,825,134 B2 | 9/2014 | Danehorn | |
| 8,918,158 B2 | 12/2014 | Scharf et al. | |
| 8,934,988 B2 | 1/2015 | Persson et al. | |
| 8,948,837 B2 | 2/2015 | Harlev et al. | |
| 8,968,299 B2 | 3/2015 | Kauphusman et al. | |
| 8,979,839 B2 | 3/2015 | De La Rama et al. | |
| 8,989,842 B2 | 3/2015 | Li et al. | |
| 9,011,423 B2 | 4/2015 | Brewster et al. | |
| 9,026,196 B2 | 5/2015 | Curran et al. | |
| 9,031,642 B2 | 5/2015 | Ghosh | |
| 9,037,259 B2 | 5/2015 | Mathur | |
| 9,044,245 B2 | 6/2015 | Condie et al. | |
| 9,167,982 B2 | 10/2015 | Scharf et al. | |
| 9,186,081 B2 | 11/2015 | Afonso et al. | |
| 9,186,212 B2 | 11/2015 | Nabutovsky et al. | |
| 9,192,318 B2 | 11/2015 | Scharf et al. | |
| 9,220,432 B2 | 12/2015 | Bukhman | |
| 9,241,687 B2 | 1/2016 | McGee | |
| 9,351,789 B2 | 5/2016 | Novichenok et al. | |
| D758,596 S | 6/2016 | Perryman et al. | |
| 9,380,953 B2 | 7/2016 | Houben et al. | |
| 9,474,486 B2 | 10/2016 | Eliason et al. | |
| 9,480,525 B2 | 11/2016 | Lopes et al. | |
| 9,486,355 B2 | 11/2016 | Gustus et al. | |
| 9,492,227 B2 | 11/2016 | Lopes et al. | |
| 9,492,228 B2 | 11/2016 | Lopes et al. | |

(56) References Cited

U.S. PATENT DOCUMENTS

| | | |
|---|---|---|
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,686 S | 3/2017 | Werneth et al. |
| 9,585,588 B2 | 3/2017 | Marecki et al. |
| 9,603,651 B2 | 3/2017 | Ghosh |
| 9,610,024 B2 | 4/2017 | Scharf et al. |
| 9,675,266 B2 | 6/2017 | Afonso et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,757,044 B2 | 9/2017 | Scharf et al. |
| 9,827,039 B2 | 11/2017 | Dandler et al. |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,082,395 B2 | 9/2018 | Koyrakh et al. |
| 2001/0007070 A1 | 7/2001 | Stewart et al. |
| 2002/0026118 A1 | 2/2002 | Govari |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0153907 A1 | 8/2003 | Suorsa et al. |
| 2003/0158477 A1 | 8/2003 | Panescu |
| 2003/0176799 A1 | 9/2003 | Beatty et al. |
| 2003/0231789 A1 | 12/2003 | Willis et al. |
| 2003/0236466 A1* | 12/2003 | Tarjan .................. A61B 5/0408 600/508 |
| 2004/0039312 A1 | 2/2004 | Hillstead et al. |
| 2004/0082948 A1 | 4/2004 | Stewart et al. |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0287777 A1 | 11/2008 | Li et al. |
| 2009/0024086 A1 | 1/2009 | Zhang et al. |
| 2009/0076483 A1 | 3/2009 | Danehorn |
| 2009/0131930 A1 | 5/2009 | Gelbart et al. |
| 2009/0143651 A1 | 6/2009 | Kallback et al. |
| 2009/0171274 A1 | 7/2009 | Harlev et al. |
| 2009/0264781 A1* | 10/2009 | Scharf .................. A61B 5/042 600/509 |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0256627 A1 | 10/2010 | Ma et al. |
| 2010/0286551 A1 | 11/2010 | Harlev et al. |
| 2010/0298690 A1* | 11/2010 | Scharf .................. A61B 5/0422 600/407 |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172859 A1 | 7/2012 | Condie et al. |
| 2012/0184863 A1 | 7/2012 | Harlev et al. |
| 2012/0271138 A1 | 10/2012 | Kordis et al. |
| 2012/0271139 A1 | 10/2012 | Kordis et al. |
| 2012/0310064 A1 | 12/2012 | McGee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf et al. |
| 2014/0235988 A1 | 8/2014 | Ghosh |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0038862 A1 | 2/2015 | Gijsbers et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2017/0035486 A1 | 2/2017 | Lopes et al. |
| 2017/0100049 A1 | 4/2017 | Scharf et al. |
| 2017/0202469 A1 | 7/2017 | Scharf et al. |
| 2017/0258347 A1 | 9/2017 | Scharf et al. |
| 2017/0311833 A1 | 11/2017 | Afonso et al. |
| 2017/0319180 A1 | 11/2017 | Henneken et al. |
| 2018/0055374 A1 | 1/2018 | Scharf et al. |
| 2018/0146948 A1 | 5/2018 | Chou et al. |

FOREIGN PATENT DOCUMENTS

| | | |
|---|---|---|
| CN | 201275144 | 7/2009 |
| EP | 1166714 | 1/2002 |
| EP | 1760661 | 3/2007 |
| EP | 1779787 | 5/2007 |
| EP | 2051625 | 4/2009 |

(56) References Cited

FOREIGN PATENT DOCUMENTS

| | | |
|---|---|---|
| EP | 2252203 | 11/2010 |
| EP | 2683293 | 1/2014 |
| JP | 08501477 | 2/1996 |
| JP | 10137207 | 5/1998 |
| JP | 2000510030 | 8/2000 |
| JP | 2001070269 | 3/2001 |
| JP | 2002051998 | 2/2002 |
| JP | 2002113004 | 4/2002 |
| JP | 2002522106 | 7/2002 |
| JP | 2003511098 | 3/2003 |
| JP | 2004350702 | 12/2004 |
| JP | 2005536313 | 12/2005 |
| JP | 2006-511296 | 4/2006 |
| JP | 2008149132 | 7/2008 |
| JP | 2011504363 | 2/2011 |
| JP | 2011507656 | 3/2011 |
| JP | 2014506171 | 3/2014 |
| WO | 199406349 | 3/1994 |
| WO | 199905971 | 2/1999 |
| WO | 200007501 | 2/2000 |
| WO | 200245608 | 6/2002 |
| WO | 2002045608 | 6/2002 |
| WO | 2003026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | WO 2009090547 A2 * | 7/2009 ........... A61B 5/0422 |
| WO | 2011136867 | 11/2011 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2014124231 | 2/2013 |
| WO | 2014036439 | 3/2014 |
| WO | 2014130169 | 8/2014 |
| WO | 2015148470 | 10/2015 |
| WO | 2017192769 | 11/2017 |

OTHER PUBLICATIONS

Patent Examination Report No. 2 dated Jun. 14, 2018 in related Australian Application No. 2014214756.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Office Action dated Mar. 9, 2016 in corresponding European Patent Application No. 09702094.5.
Partial European Search Report dated Apr. 29, 2014 in corresponding European Application No. 13176658.
Patent Examination Report No. 3 dated Sep. 21, 2016 in related Australian Application No. 2012225250.
Pullan et al. "The inverse problem of electrocardiology" Northeastern University Electrical and Computer Engineering, Feb. 23, 2007.
Van Oosterom A: "Solidifying the solid angle." 2002 Journal of Electrocardiology 2002 vol. 35 Suppl pp. 181-192 ISSN: 0022-0736.
Japanese Office Action dated Feb. 16, 2016 issued in corresponding Japanese Application No. 2013-557-926, with English language summary.
Japanese Notice of Allowance Jul. 11, 2017 issued in corresponding Japanese Application No. 2013-557-926, with English language summary.
Office Action dated Apr. 27, 2016 in corresponding Canadian Application No. 2,747,859.
Anoop Kumar Gupta, et al., "Point of View Cardiac Mapping: Utility or Futility?", Non-contact Endocardial Mapping Indian Pacing and Electrophysiology Journal, vol. 2, No. 1, Jan. 1, 2002, pp. 20-32 XP055128732.

Christoph Scharf, et al. Declaration under 37 C.F.R. 1.132, Nov. 15, 2012.
Australian Office Action dated Feb. 26, 2018 issued in Australian Application No. 2017201560.
Australian Office Action dated Mar. 17, 2018 issued in corresponding Australian Application No. 2013308531.
Canadian Office Action dated Apr. 26, 2017 issued in corresponding Canadian Application No. 2932956.
Canadian Office Action dated Jan. 22, 2018 issued in corresponding Canadian Application No. 2932956.
Canadian Office Action dated Mar. 30, 2017 issued in corresponding Canadian Application No. 2747859.
Canadian Office Action dated Nov. 27, 2017 issued in corresponding Canadian Application No. 2829626.
Chinese Office Action dated Apr. 17, 2017 issued in corresponding Chinese Application No. 201480018328.4.
Decision dated Jan. 16, 2018 issued for European Patent Application No. 09702094.5.
Decision dated Jan. 18, 2018 issued for European Patent Application No. 13176658.6.
International Search Report in related Application No. PCT/IB2009/000071 dated Oct. 7, 2009.
European Office Action dated Apr. 28, 2014, issued in corresponding European Application No. 09 702 094.5-1660.
European Office Action dated Feb. 29, 2016 issued in corresponding European Application No. 07 785 075.8-1657.
European Office Action dated Jan. 31, 2018, issued in corresponding European Application No. 13763151.1.
European Office Action dated Mar. 21, 2017 issued in corresponding European Application No. 07785075.8.
Extended European Search Report dated Mar. 14, 2017 issued in corresponding European Application No. EP14843283.4.
Extended European Search Report dated Oct. 18, 2017, issued in European Application No. 15768711.
International Search Report and Written Opinion dated Aug. 4, 2017 issued in corresponding International Application No. PCT/US17/30915.
International Search Report and Written Opinion dated Dec. 12, 2017 issued in corresponding International Application No. PCT/US2017/056064.
International Search Report and Written Opinion dated Jun. 26, 2015 issued in International Application No. PCT/US2015/022187.
International Search Report and Written Opinion dated Sep. 25, 2017, issued in corresponding Application No. PCT/US17/30922.
International Search Report dated Mar. 10, 2015 issued in corresponding International Application No. PCT/US14/54942.
International Search Report dated Apr. 21, 2008 in related International Application No. PCT/CH2007/000380.
Invitation to Pay Additional Fees dated Jan. 8, 2014 in corresponding International Application No. PCT/US2013/057579.
ISRWO dated Aug. 8, 2016 issued in corresponding European Application No. PCT/US2016/031823.
ISRWO dated Aug. 11, 2016 dated in corresponding International Application No. PCT/US2016/032017.
ISRWO dated Aug. 18, 2016 issued in corresponding International Application No. PCT/US16/32420.
ISRWO dated May 20, 2014 in International application No. PCT/US14/15261.
Japanese Notice of Allowance dated Feb. 27, 2018 issued in corresponding Japanese Application No. 2015-530101, with English language translation.
Japanese Office Action dated Jan. 31, 2017 issued in corresponding Japanese Application No. 2013-557-926, with English language summary.
Japanese Office Action dated Jun. 27, 2017 issued in corresponding Japanese Application No. 2015-530101, with English language translation.
Japanese Office Action dated Sep. 26, 2017 issued in corresponding Japanese Application No. 2017-155346, with English translation.
Office Action dated Nov. 7, 2017, issued in European Application No. 15768711.
Office Action dated Oct. 10, 2017, issued in Application No. 2015-557091 with machine translation to English.

(56) References Cited

OTHER PUBLICATIONS

Office Action dated Mar. 9, 2016 in corresponding European Patent Application No. 13176658.6.
Office Action dated May 30, 2016 in related Australian Patent Application No. 2012225250.
Office Action dated Oct. 4, 2013 in corresponding Canadian Patent Application No. 2,659,898.
PCT ISRWO dated Jun. 5, 2014, issued in corresponding PCT Application No. PCT/US2013/057579.
Della Bella et al. "Non-contact mapping to guide catheter ablation of untolerated ventrical tachycardia" European Heart Journal, May 2002, 23(9)742-752.
Examination report dated Jul. 6, 2017 issued in Australian Patent Application No. 2014214756.
Examination Report dated Jun. 27, 2017 issued in Australian Application No. 2013308531.
Examiner's Report dated Dec. 22, 2015 in related Canadian Application No. 2656898.
Extended European Search Report for related Application No. 13176658 dated Sep. 29, 2014.
Extended European Search Report dated Jul. 8, 2016 in related European Application No. 14748567.6.
He et al. "An equivalent body surface charge model representing three-dimensional bioelectrical activity" IEEE Transactions on Biomedical Engineering, 42.7 (Jul. 7, 1995) pp. 637-646.
International Search Report and Written Opinion in related Application No. PCT/US2012/028593 dated Mar. 5, 2013.
Wolfgang Nolting: Elektrodynamik—Grundkurs Theoretische Physik 3, Springer Spectrum, Feb. 28, 2016, p. 89-91, XP009188752.
William G. Stevenson et al: "Recording Techniques for Clinical Electrophysiology" Journal of Cardiovascular Electrophysiology. vol. 16 No. 91, Sep. 2005, pp. 1017-1022.
Canadian Office Action dated Oct. 29, 2018 issued in corresponding Canadian Application No. 2829626.
Japanese Office Action dated Aug. 28, 2018 issued in corresponding Japanese Application No. 2016-542062, with machine translation into English.
Canadian Office Action dated Nov. 7, 2018 issued in corresponding Canadian Application No. 2932956.
Japanese Office Action dated Dec. 11, 2018 issued in corresponding Japanese Application No. 2018-024907, with machine translation to English.
Australian Examination Report dated Jun. 28, 2018, issued in corresponding Australian Patent Application No. 2014318872.
Japanese Notice of Allowance dated Sep. 18, 2018 issued in corresponding Japanese Application No. 2015-557091, with English language translation.
Extended European Search Report dated Dec. 5, 2018 issued in corresponding European Application No. 16793622.8.
Extended European Search Report dated Oct. 4, 2018 issued in corresponding European Application No. 16793503.0.
Australian Office Action dated Jan. 26, 2019 issued in corresponding Australian Application No. 2018211348.
Japanese Notice of Allowance dated Mar. 5, 2019 issued in corresponding Japanese Application No. 2018061040, with English translation.
Australian Examination Report dated Feb. 8, 2019 issued in corresponding Australian Application No. 2018250516.
European Office Action dated Jan. 28, 2019 issued in corresponding European Application No. 14748567.6.
Japanese Office Action dated Feb. 19, 2019 issued in corresponding Japanese Application No. 2016-558799, with machine translation to English.
European Office Action dated Feb. 6, 2019 issued in corresponding European Application No. 14843283.4.
International Search Report and Written Opinion dated Apr. 8, 2019, issued in corresponding International Application No. PCT/USI9/14498.

\* cited by examiner

DEVICE AND METHOD FOR THE GEOMETRIC DETERMINATION OF ELECTRICAL DIPOLE DENSITIES ON THE CARDIAC WALL

CROSS REFERENCE TO RELATED APPLICATIONS

The present application is a continuation application of U.S. patent application Ser. No. 15/672,020, filed Aug. 8, 2017, which is a continuation of U.S. patent application Ser. No. 14/003,671, filed Sep. 6, 2013 (now U.S. Pat. No. 9,757,044) which is a 371 national stage application of Patent Cooperation Treaty Application No. PCT/US2012/028593 filed Mar. 9, 2012, entitled DEVICE AND METHOD FOR THE GEOMETRIC DETERMINATION OF ELECTRICAL DIPOLE DENSITIES ON THE CARDIAC WALL, which in turn claims priority under 35 USC 119(e) from U.S. Provisional Patent Application 61/451,357 filed Mar. 10, 2011, entitled DEVICE AND METHOD FOR THE GEOMETRIC DETERMINATION OF ELECTRICAL DIPOLE DENSITIES ON THE CARDIAC WALL, the disclosures of which are incorporated herein by reference in their entireties.

FIELD OF THE INVENTION

The present invention relates generally to the localization and treatment of cardiac arrhythmias, and more particularly to devices and methods for real time, non-contact imaging and distance measurements using ultrasound for dipole density mapping, as well as methods for diagnosing tissue health.

BACKGROUND OF THE INVENTION

Systems used to localize the origin of cardiac arrhythmias measure potentials (e.g. in millivolts) in the cardiac chambers and localize them on a three dimensional representation of the cardiac chamber wall. The measurement of the electrical activity present on the cardiac walls is called mapping. For this purpose, a multiple electrode mapping catheter may be positioned within the heart such that multiple potentials can be simultaneously measured at different locations on the wall of the cardiac chamber without having direct wall contact (non-contact mapping). The cardiac chamber is visualized as a three dimensional structure, either directly by moving one or more mapping electrodes within the corresponding heart chamber or by importing an anatomical geometry of the cardiac chamber from an imaging device (e.g. Computed Tomography, MRI, or ultrasound). The electrical activity within the heart can be measured with the multi-electrode mapping catheter, which may be able to simultaneously measure potentials at different points in three dimensional space. In the current systems, the measured potentials from the non-contact multi-electrode mapping catheter do not directly correspond to the electrical activity on the cardiac wall as measured with an electrode with direct wall contact (contact mapping). The measured potentials of the non-contact mapping system have to be converted with computer programs and extrapolated into virtual electrograms projected on the heart chamber of the mapping system.

U.S. Pat. No. 5,297,549 (Beatty, et al.) discloses a method of generating a three-dimensional map of electrical activity in a heart chamber as well as a two-dimensional map of the electrical activity within the endocardial surface. Beatty generates the information via an array of electrodes placed in a heart chamber utilizing impedance plethysmography, while one electrode serves as a reference.

The current conversion methods suffer various instabilities, and further processing, termed regularization, must be applied to maintain stability. Regularization decreases spatial resolution. Another limitation of the current methods is that the provided potentials represent only the mean electrical activity summed across a large region of tissue, with cells consisting of membranes separating electrical dipoles.

Since the localization of cardiac arrhythmias by the use of potentials is imprecise, the successful treatment of cardiac arrhythmias has been difficult and has demonstrated limited success and reliability. There is, therefore, a need for improved methods of localizing cardiac arrhythmias.

SUMMARY

The present invention discloses devices and methods for real time, non-contact imaging and distance measurements using ultrasound for dipole density mapping, as well as methods for diagnosing tissue health. In one aspect, the present invention includes a device comprising one or more catheters, each catheter comprising a shaft. The shaft may include a lumen and may be steerable. The shaft may include, typically near its distal end, one or more components selected from group consisting of: electrodes, such as electrodes configured to record electrical activity of tissue; transducers such as ultrasound transducers; sensors, such as ultrasound sensors; ultrasound crystals configured to both transmit and sense ultrasound waves; and combinations of these. The device is constructed and arranged to produce continuous, real-time images of a patient's tissue, as well as information related to electrical activity present in the tissue. For example, a user, such as a clinician may image a patient's cardiac chamber, including the cardiac walls. The device is also capable of providing tissue information, for example, tissue movement and tissue thickness. Additionally, the device is configured to produce distance measurements by analyzing at least one of the sensors recorded angles or frequency changes. Non-limiting examples of distance measurements include: distance between the multiple electrodes and the wall of the cardiac chamber and distance between the multiple electrodes and the transducer and/or sensor. The device may be configured to provide a tissue diagnostic through an analysis of both tissue motion information and cell electrical signals. The cell electrical signals may be recorded by the multiple electrodes, while tissue motion information may be gathered by the multiple electrodes and/or the sensor. The device is configured to provide exact foci and conduction-gap position information, such that ablation is performed with an increased level of precision. Small conduction paths, including "gaps" in a line, are equally relevant as foci. The device may include an ablation catheter, such as an ablation catheter that can be precisely delivered through an open lumen of a second device catheter, or through a sheath.

In some embodiments, the device may include a catheter which is further configured as a delivery sheath. For example, a first catheter may comprise a lumen, such that a separate ablation catheter may be slidingly received by the first catheter. Additionally, a single sheath may be provided to allow the first catheter and the ablation catheter to pass there though. This construction would eliminate the need for multiple sheath devices.

In some embodiments, one or more catheters of the device may be steerable. For example, a user may determine the ablation site via real-time tissue analysis and imaging, and subsequently a catheter may be steered to the desired location. Steering of one or more catheters may be achieved via cables, such as cables which may be housed in a lumen of a delivery sheath.

The device comprises a transducer, preferably an ultrasound transducer configured to produce sound waves, typically at a frequency between 5 and 18 MHz. The sound waves may be at a constant rate or provided in a pulsed manner. The device may comprise multiple transducers. One or more transducers may be positioned on one or more catheters of the device, such as on or near a distal portion of a catheter. One or more transducers may be further configured as sensors, such as ultrasound crystals that both record and emit sound waves.

The device comprises a sensor, preferably an ultrasound sensor configured to receive the sound waves produced by the ultrasound transducer. The device may comprise multiple sensors. One or more sensors may be positioned on one or more catheters of the device, such as on or near a distal portion of a catheter. One or more sensors may be further configured as transducers, such as ultrasound crystals that both record and emit sound waves.

The sensors, transducers, or combination sensor/transducers may be positioned on the device in various locations including but not limited to: attached to the shaft of the catheter; housed within the shaft of the catheter, for example, the sensor and/or transducer may be slidingly received by the shaft; at the geometric center of each of the multiple electrodes; proximate to at least one of the multiple electrodes; mounted to a multiple arm assembly; and combinations of these. The device may include one or more electrodes configured to record electrical activity in the tissue of cells. Various ratios of electrodes to sensors, transducers, or combination sensor/transducers may be included. In one embodiment, a ratio of two electrodes to one ultrasound crystal is provided, such as a single component with one ultrasound crystal and an electrode positioned at each end of the crystal. In another embodiment, a ratio of five electrodes to two sensor/transducers is provided, such as a catheter shaft including two assemblies and a single electrode. Each assembly includes an ultrasound crystal with an electrode positioned at each end.

The transducer and/or the sensor may be rotated, which may include a partial rotation or a full 360° rotation. Alternatively or additionally, the sensor and/or transducer may be translated along a linear axis. In one embodiment, the sensor and/or transducer comprise a piezoelectric film. For example, a wire may be electrically connected to a first electrode where a portion of the wire comprises a piezoelectric film. Alternatively, the sensor and/or transducer may comprise a piezoelectric cable.

In some embodiments, the sensor and transducer may comprise a single component, for example, a single crystal. Alternatively, the sensor and/or transducer may comprise an array of components, for example, a circumferential array of ultrasound crystals. Each of the ultrasound crystals may be attached to one or more electrodes configured to record electrical activity of living cells.

The device further comprises a first receiver that receives mapping information from multiple electrodes included in one or more catheters configured to perform mapping of cellular electrical activity, such as electrocardiogram activity. The electrodes are placed in a cardiac chamber of the patient's heart. The device further includes a second receiver that receives anatomical information. The anatomical information may be a generic heart model, or more preferably tissue contour and other anatomical information recorded from the patient's own heart. A dipole density module determines the database of dipole densities, in the table form $d(y)$, where y represents the three-dimensional location on the heart tissue including that particular dipole density. The potential at various other locations x, within a cardiac chamber and termed $V(x)$, are recorded by the multiple electrodes. Solid angle $\omega(x,y)$ represents the solid angle for a triangle projection between location x (electrode location in chamber) and y (triangle location on chamber wall). The dipole density module determines the dipole density for individual triangle shaped projections onto the cardiac chamber wall based on the following: each triangle projection at location y contributes $\omega(x,y)$ times the dipole density $d(y)$ to the potential $V(x)$ at the point x.

In a preferred embodiment, the device comprises a software program, e.g., such as a software program loaded onto a personal computer; an ECG system; a cardiac tissue ablation system and/or an imaging system. The number of triangles determined by the dipole density module is sufficiently large (triangle area small enough) such that the dipole density for each triangle projection is relatively constant. Typically 1000 or more triangles are used in the calculations, such as a calculation based on a standard sized Left or Right Atrium. Larger numbers of triangles are used for larger sized chambers.

In another preferred embodiment, the patient is being diagnosed and/or treated for a heart condition, such as an arrhythmia. The electrodes are included at the distal end of one or more mapping catheters and are placed into a chamber of the patient's heart to record potentials. An imaging instrument, such as an instrument that provides a generic model of a heart, or an instrument which provides an anatomical model of the patient's heart, delivers the anatomical information to the second receiver. In one embodiment, the imaging instrument is one or more of: Computed Tomography; MRI; ultrasound; and an ECG system with mapping catheter. Alternatively or additionally, an imaging instrument may be integrated into the device, such as an ultrasound unit configured to produce image and distance information from signals received from one or more ultrasound sensors.

In another preferred embodiment, the dipole density module implements an algorithm configured to assist in the creation of the database of dipole densities. The algorithm may be a progressive algorithm configured to be modified or refined to improve spatial and/or time resolution of the database. The dipole density module may determine a map of dipole densities at corresponding time intervals. A synthesis of maps represents a cascade of activation sequences of each corresponding heart beat.

In another preferred embodiment, the device includes a third receiver. The third receiver collects mapping information from one or more skin electrodes. The dipole density module uses the skin electrode signals to calculate or recalculate the database of dipole densities, using equations listed herebelow.

According to another aspect of the invention, a system for creating a database of dipole densities at the surface of one or more cardiac chambers of a patient's heart is provided. In addition to the device of the present invention, the system includes one or more multiple electrode catheters; an ablation device; at least one surface or skin electrode; a transducer; and a sensor. A separate imaging instrument may be included in the system. In a preferred embodiment, the mapping catheter is also used for ablating tissue identified by the database of dipole densities and positioned in the heart chamber using the real-time imaging. The system includes a monitor to display the real-time image and dipole density information, such as information displayed in relative geometry to the chamber of the patient's heart.

According to another aspect of the invention, a method of creating a database of dipole densities at the surface of one or more cardiac chambers of a patient's heart is provided. The method can be used to diagnose and/or treat complex cardiac arrhythmia disease. In a typical configuration, complex electrograms are identified, such as a method in which three or more complex electrograms are identified. In a preferred embodiment, the method is used to diagnose and/or treat Atrial Fibrillation (AF), Ventricular Tachycardia (VT), Atrial Flutter and tissue scarring, such as tissue scarring caused by an intra-cardiac defibrillator (ICD). In another preferred embodiment, the method is used to detect ventricular ischemia and/or quantify myocardial function. The method includes placing an array of multiple electrodes within a chamber of the patient's heart to measure potentials and calculating the distance or movement information by analyzing signals received from a sound sensor. The array of multiple electrodes may or may not be repositioned to determine dipole densities.

In another preferred embodiment, the method further includes placing one or more skin electrodes. The information recorded by the skin electrodes is used to determine the database of dipole densities. In yet another embodiment, the method further comprises calculating tissue thickness information.

According to another aspect of the invention, a medical method for obtaining electrical and anatomical information related to a patient's cardiac chamber(s) is disclosed. In a first step, a user may insert a device into a delivery system. The device may be any device described hereabove. In a next step, the user may advance the device through the delivery system and into a heart chamber. In a next step the device and/or delivery system may be steered such that the distal end of the device is positioned approximately in the geometric center of the heart chamber. Once the device is positioned within the heart chamber, measurements may be obtained and analyzed consistent with measurements and methods disclosed herein.

According to another aspect of the invention, a method for diagnosing tissue is disclosed. The preferred method comprises placing a distal end of an electrode catheter into one or more cardiac chambers of a patient, where the electrode catheter comprises at least one electrode and at least one ultrasound element. In a next step, anatomical information, such as tissue movement, may be determined via the at least one ultrasound element. In a next step, the electrical charge of a tissue may be determined via the at least one electrode. Lastly, by analyzing tissue movement and electrical charge information, tissue health may be determined.

For example, electrical information indicative of adequate electrical activity and anatomical information indicative of adequate tissue motion correlates to presence of healthy tissue. Additionally, electrical information indicative of adequate electrical activity and anatomical information indicative of inadequate tissue motion correlates to presence of at least one of ischemic tissue or hibernating tissue. Conversely, electrical information indicative of inadequate electrical activity and anatomical information indicative of inadequate tissue motion correlates to presence of scar tissue. Additionally, electrical information indicative of inadequate electrical activity and anatomical information indicative of inadequate tissue motion correlates to presence of a complete ablation, such as an ablation performed in a cardiac ablation performed to treat a cardiac arrhythmia. In some embodiments, the complete ablation comprises a transmural ablation.

More specifically, the following four cases may exist:
Case 1: Electrical and anatomical are adequate—Tissue is healthy,
Case 2: Electrical is adequate and anatomical is inadequate—Tissue is compromised,
Case 3: Electrical is inadequate and anatomical is adequate—Tissue is compromised, and
Case 4: Electrical and anatomical are both inadequate—Tissue necrosis.

The actual threshold for determining adequacy of electrical function of any one area of the heart is dependent upon many factors, including the degree of coordination of the activation pattern and the mass of the cells being activated. Additionally, this threshold will be different for each chamber of the heart as well as from smaller to larger patients. For example, a threshold of 0.5 mV may be appropriate, wherein an electrical potential smaller that 0.5 mV may be indicative of inadequate electrical function and an electrical potential at or larger than 0.5 mV may be indicative of adequate electrical function.

Also included in the tissue diagnostic, a clinician may assess the electrical integrity of the cardiac cells. For example, the functional status of the cardiac cells may be assessed.

In one embodiment, the electrical information comprises dipole density information. Additionally or alternatively, the electrical information may comprise at least one of repolarization or speed of wave-front propagation.

The method may further comprise ablating the cardiac tissue based upon the tissue diagnosis. For example, the anatomical information comprises tissue thickness information and at least one of the ablation energy or the time period is adjusted based on the tissue thickness information. A clinician may assess the tissue during and post ablation to assess changes in the tissue due to the application of the ablation energy. For example, the clinician may also use information received form one or more ultrasound sensors in combination with dipole density mapping information received from one or more electrodes to assess the adequacy of tissue ablation, such as to improve long-term patient outcomes.

In accordance with an aspect of the present invention, provided is a device for creating a database of dipole densities d(y) and distance measurements at the surface of one or more cardiac chambers of a patient. The device comprise: multiple electrodes located on one or more catheters; a transducer constructed and arranged to emit sound waves; and a sensor constructed and arranged to receive reflections of the sound waves.

In various embodiments, the transducer can comprise the sensor.

In various embodiments, the transducer can further comprise at least one of the multiple electrodes.

In various embodiments, the device can be constructed and arranged to produce a real time image.

In various embodiments, the device can be constructed and arranged to produce continuous images.

In various embodiments, the device can be constructed and arranged to produce images of the patient's tissue.

In various embodiments, the image can comprise an image of the one or more cardiac chambers.

In various embodiments, the image can comprises an image of a wall of the one or more cardiac chambers.

In various embodiments, the image can comprise an image of tissue proximate at least one of the multiple electrodes.

In various embodiments, image can comprise an image of at least one of the multiple electrodes.

In various embodiments, the device can be constructed and arranged to provide motion information of the patient's tissue.

In various embodiments, the motion information can comprise cardiac wall motion information.

In various embodiments, the device is constructed and arranged to provide thickness information of the patient's tissue.

In various embodiments, the thickness information can be cardiac wall thickness information.

In various embodiments, the device can be constructed and arranged to produce an image of at least one of the multiple electrodes.

In various embodiments, the device can be constructed and arranged to further produce an image of tissue proximate at least one of the multiple electrodes.

In various embodiments, the device can be constructed and arranged to further produce an image of the one or more cardiac chambers.

In various embodiments, the device can be constructed and arranged to produce a distance measurement.

In various embodiments, the distance measurement can comprise the distance between at least one of the multiple electrodes and a wall of a cardiac chamber.

In various embodiments, the distance measurement can comprise the distance between at least one of the multiple electrodes and at least one of the transducer or the sensor.

In various embodiments, the distance measurement can comprise the distance between a wall of a cardiac chamber and at least one of the transducer or the sensor.

In various embodiments, the device can be constructed and arranged to produce the distance measurement by analyzing at least one of sensor recorded angle or frequency changes.

In various embodiments, the device can be constructed and arranged to determine the position of at least one of the multiple electrodes within a cardiac chamber.

In various embodiments, the device can be constructed and arranged to determine the position of at least two of the multiple electrodes within the cardiac chamber.

In various embodiments, the device can be constructed and arranged to combine distance information received from the multiple electrodes with information received from the sensor. p In various embodiments, the device can be constructed and arranged to provide tissue diagnostic information by analyzing both tissue motion information and cell electrical signals.

In various embodiments, the cell electrical signals can be recorded by the multiple electrodes.

In various embodiments, the tissue motion information can be provided by the sensor.

In various embodiments, the tissue motion information can be further provided by the multiple electrodes.

In various embodiments, the device can be constructed and arranged to provide the tissue diagnostic information during a cardiac ablation procedure.

In various embodiments, the device can be constructed and arranged to provide tissue diagnostic information while arrhythmia therapy or functional therapy is being delivered, wherein such arrhythmia therapy and functional therapy include, but are not limited to, the following therapies: ablation, genetic-agent delivery, Cardiac Resynchronization, and pharmacologic.

In various embodiments, the device can be constructed and arranged to deliver ablation energy to tissue.

In various embodiments, the device can be constructed and arranged to provide precise foci, conduction-gaps, or conduction channels position information.

In various embodiments, the device can be constructed and arranged to locate foci, boundaries of conduction-gaps, or boundaries of conduction channels position within 1 mm to 3 mm The device of any other claim herein, wherein the device can be constructed and arranged to provide the location of cardiac tissue with complex electrograms.

In various embodiments, the device can be constructed and arranged to provide at least three locations comprising complex electrograms.

In various embodiments, the device can be constructed and arranged to provide single beat mapping of cardiac arrhythmias In various embodiments, the device can comprise at least one catheter that is constructed and arranged to be steered and/or guided.

In various embodiments, the catheter can be constructed and arranged to be steered and/or guided to the sites of complex electrograms by the real-time tissue analysis and imaging.

In various embodiments, the device can further comprise a delivery sheath.

In various embodiments, the delivery sheath can be constructed and arranged to slidingly receive an ablation catheter.

In various embodiments, the device can further comprise an elongate shaft, comprising a proximal portion with a proximal end and a distal portion with a distal end constructed and arranged to be inserted into the body of the patient.

In various embodiments, device can further comprise a clamp assembly constructed and arranged to be removably attached to the elongate shaft and to transmit vibrational energy.

In various embodiments, the clamp assembly can comprise a vibrational transducer configured to emit ultrasound waves.

In various embodiments, the clamp assembly can comprise a clamping mechanism constructed and arranged to be removably attached to the elongate shaft.

In various embodiments, the clamp assembly can be positioned on the proximal portion of the elongate shaft.

In various embodiments, the device can further comprise a handle wherein the proximal portion is within 10 centimeters from the handle.

In various embodiments, the elongate shaft can further comprise a conduit constructed and arranged to transmit the ultrasound waves from the proximal portion to the distal portion.

In various embodiments, the clamp assembly can be positioned on the distal portion of the elongate shaft.

In various embodiments, the distal portion can be within 10 centimeters from the distal end of the elongate shaft.

In various embodiments, the device can further comprise multiple electrodes wherein the multiple electrodes are positioned on the distal end of the elongate shaft and the clamp assembly is constructed and arranged to vibrate the multiple electrodes.

In various embodiments, the multiple electrodes can comprise the multiple electrodes described above.

In various embodiments, the device can further comprise at least one thermocouple positioned on the elongate shaft wherein the clamp assembly is constructed and arranged to vibrate the at least one thermocouple.

In various embodiments, the device can further comprise at least one support arm attached to the elongate shaft wherein the clamp assembly is constructed and arranged to vibrate the at least one support arm.

In various embodiments, the device can comprise at least one support arm comprises at least one of a sensor or a transducer.

In various embodiments, the device can further comprise at least one ablation element attached to the elongate shaft wherein the clamp assembly is constructed and arranged to vibrate the at least one ablation element.

In various embodiments, the device can further comprise at least one sensor attached to the elongate shaft wherein the clamp assembly is constructed and arranged to vibrate the at least one sensor where the sensor is selected from the group consisting of: temperature; pressure; electrical signal; electrode; sound; and combinations of these.

In various embodiments, the device can further comprise at least one transducer attached to the elongate shaft wherein the clamp assembly is constructed and arranged to vibrate the at least one transducer where the transducer is selected from the group consisting of: ablation element; electrode; sound; and combinations of these.

In various embodiments, the device can further comprise at least one ultrasound crystal positioned on the elongate shaft wherein the clamp assembly is constructed and arranged to vibrate the at least one crystal.

In various embodiments, the clamp assembly can be constructed and arranged to vibrate the elongate shaft.

In various embodiments, the clamp assembly can be positioned such that the clamp assembly is located outside the patient's body while the distal end of the elongate shaft is located within the patient's body.

In various embodiments, at least one of the sensor or the transducer can be constructed and arranged to clamp to a shaft.

In various embodiments, the device can comprise a shaft and at least one of the sensor or the transducer is constructed and arranged to clamp to said device shaft.

In various embodiments, at least one of the sensor or the transducer can be constructed and arranged to be slidingly received by a shaft.

In various embodiments, at least one of the sensor or the transducer can be constructed and arranged to be positioned at a geometric center of the multiple electrodes.

In various embodiments, at least one of the sensor or the transducer can comprise a single component.

In various embodiments, the single component can comprise a single crystal.

In various embodiments, at least one of the sensor or the transducer can be constructed and arranged to be rotated.

In various embodiments, at least one of the sensor or the transducer can be constructed and arranged to be rotated 360°.

In various embodiments, at least one of the sensor or the transducer can be constructed and arranged to be translated along an axis.

In various embodiments, at least one of the sensor or the transducer can comprises an array of components.

In various embodiments, the array can comprise an array of ultrasound crystals.

In various embodiments, the array can comprise a circumferential array.

In various embodiments, at least one of the sensor or the transducer can be positioned in or proximate to at least one of the multiple electrodes.

In various embodiments, at least one of the sensor or the transducer can comprise a first component and a second component and wherein the first component is mounted in or proximate to a first electrode of the multiple electrodes and the second component is mounted in or proximate to a second electrode of the multiple electrodes.

In various embodiments, at least one of the sensor or the transducer can comprise piezoelectric film.

In various embodiments, the device can further comprise a wire electrically connected to a first electrode and wherein the piezoelectric film covers at least a portion of said wire.

In various embodiments, at least one of the sensor or the transducer can comprise piezoelectric cable.

In various embodiments, the device can comprise a multiple arm assembly and wherein the at least one of the sensor or the transducer is mounted to the multiple arm assembly.

In various embodiments, a first electrode of the multiple electrodes can be mounted to the multiple arm assembly.

In various embodiments, at least one of the sensor or the transducer can be integral to at least one electrode of the multiple electrodes.

In various embodiments, at least one of the sensor or the transducer can comprise a first surface, and wherein at least one electrode of the multiple electrodes can comprise a second surface, and wherein the first surface and the second surface are parallel.

In various embodiments, at least one of the sensor or the transducer can be constructed and arranged to rotate and transmit or receive signals to or from the cardiac chamber.

In various embodiments, the transducer can comprise an ultrasound transducer.

In various embodiments, the transducer can be constructed and arranged to produce sound waves in at least one of either constant or pulsed excitation.

In various embodiments, the transducer can comprise multiple transducers.

In various embodiments, the transducer can produce signals with a frequency between 3 Mhz and 18 Mhz.

In various embodiments, the transducer can be constructed and arranged to clamp on a shaft.

In various embodiments, the device can comprise a shaft and wherein the transducer is constructed and arranged to clamp on said device shaft.

In various embodiments, the sensor can comprise an ultrasound sensor.

In various embodiments, the sensor can comprise multiple sensors.

In various embodiments, the sensor can be constructed and arranged to clamp on a shaft.

In various embodiments, the device can comprise a shaft and wherein the sensor is constructed and arranged to clamp on said device shaft.

In various embodiments, the device can further comprise: a first receiver constructed and arranged to receive mapping information from the multiple electrodes, the mapping information received when the multiple electrodes are placed in the one or more cardiac chambers; a dipole density module constructed and arranged to generate the three dimensional database of dipole densities $d(y)$, wherein the dipole density module determines a dipole density for individual triangle shaped projections onto the cardiac chamber wall, where each triangle projection at a location y contributes $\omega(x,y)$ times the dipole density d(y) to a potential V(x) at a point x. Here ω(x,y) is the solid angle for that triangle projection, and where: a) x represents a series of locations within one or more cardiac chambers; and b) V(x) is a measured potential at point x, said measured potential recorded by the multiple electrodes.

In various embodiments, the device further comprise: a second receiver constructed and arranged to receive anatomical information from at least one imaging instrument configured to produce a geometrical depiction of the one or more cardiac chambers.

In various embodiments, said triangle projections can be sized such that the dipole density for each triangle projection is substantially constant.

In various embodiments, the dipole density can be determined for at least 1000 triangle shaped projections.

In various embodiments, the dipole density can be determined by a number of triangle shaped projections, said number determined by the size of a cardiac chamber.

In various embodiments, the multiple electrodes can be included in a single catheter.

In various embodiments, the multiple electrodes can be included in two or more catheters.

In various embodiments, the imaging instrument can be selected from a group consisting of: a computed tomography (CT) instrument; a magnetic resonance imaging (MRI) instrument; an ultrasound instrument; a multiple electrode mapping catheter and mapping system; and combinations thereof.

In various embodiments, the imaging instrument can comprise a standard anatomical geometry which is uploaded to the dipole density module.

In various embodiments, the dipole density module can include a mathematical processing element that comprises one or more of: a computer; an electronic module; a computer program stored in a memory and executable by a processor; a microcontroller; a microprocessor; and combinations thereof.

In various embodiments, the dipole density module can be configured to implement a progressive algorithm configured to improve at least one of a spatial resolution and a time resolution of the database of dipole densities d(y).

In various embodiments, the dipole density module can use a linear system of equations to determine the database of dipole densities d(y).

In various embodiments, the dipole density module can be configured to determine a map of dipole densities d(y) at corresponding time intervals.

In various embodiments, the dipole density module is configured to generate a synthesis of maps that represents a cascade of activation sequences of each corresponding heart beat from a series of heart beats.

In various embodiments, a number of measured potentials V(x) can be in a range of up to 100,000 potentials V(x).

In various embodiments, the cardiac wall can be divided into regions, wherein each region is represented by a region solid angle with respect to each electrode, and wherein each region solid angle is the sum of the solid angles of the individual triangles in the region.

In various embodiments, a number of regions used to determine the dipole density d(y) can be in a range of up to 100,000 regions on the cardiac wall.

In various embodiments, the measured potentials V(x) can be interpolated to increase the number of regions.

In various embodiments, V(x) can be interpolated using splines.

In various embodiments, the device can further comprise: a third receiver configured to receive mapping information from one or more skin electrodes.

In various embodiments, the dipole density module can use said mapping information from the one or more skin electrodes to calculate and/or recalculate the database of dipole densities d(y).

In various embodiments, the dipole density module can calculate and/or recalculate the dipole densities d(y) using at least one of the following equations:

$$W_k = \sum_{l=1}^{L} A_{kl} V_l \quad (1)$$

wherein a small sinusoidal voltage Vl is applied to each electrode l=1, . . . L on the electrode array in the heart, and the resulting voltages Wk, k=1, . . . K is measured at the surface electrodes, which yields the KXL transition matrix.

$$V_l = \sum_{n=1}^{N} B_{ln} d_n \quad (2)$$

wherein calculating solid angles produces the linear transformation Bln, between the electrode array potentials Vl and the dipole densities dn, n=1, . . . N of N regions of the heart wall; and $$W_k = \sum_{l=1}^{L} \sum_{n=1}^{N} A_{kl} D_{ln} d_n \quad (3)$$

where equation (2) above is substituted into equation (1) to form equation (3).

In various embodiments, the dipole density module can be configured to solve equations (2) and (3) using regularization techniques.

In various embodiments, the regularization technique can comprise a Tikhonov regularization.

In accordance with another aspect of the invention, provided is a system for creating a database of dipole densities d(y) and distance measurements at the surface of one or more cardiac chambers of a patient. The system comprise: a device for creating a database of dipole densities d(y) at the surface of one or more cardiac chambers of a patient, comprising: multiple electrodes located on one or more catheters; a first receiver configured to receive mapping information from the multiple electrodes, the mapping information received when the multiple electrodes are placed in the one or more cardiac chambers; a second receiver configured to receive anatomical information from at least one imaging instrument configured to produce a geometrical depiction of the one or more cardiac chambers; a dipole density module configured to generate the database of dipole densities d(y), wherein the dipole density module determines a dipole density for individual triangle shaped projections onto the cardiac chamber wall, where each triangle projection at a location y contributes ω(x,y) times the dipole density d(y) to a potential V(x) at a point x, wherein ω(x,y) is the solid angle for that triangle projection, and wherein: a) x represents a series of locations within one or more cardiac chambers; and b) V(x) is a measured potential at point x, said measured potential recorded by the multiple electrodes.

In various embodiments, the system can further comprise a second imaging instrument.

In various embodiments, the system can comprise a catheter for mapping and ablation.

In various embodiments, the system can comprise an ablation device configured to deliver one or more of: radio frequency (RF) energy; ultrasound energy, and cryogenic energy.

In various embodiments, the system can comprise a device configured to deliver one or more of the following therapies: genetic-agent delivery, cardiac resynchronization, and pharmacologic.

In accordance with another aspect of the invention, provided is a method of creating a database of dipole densities d(y) and distance measurements at the surface of one or more cardiac chambers of a patient. The method comprises: placing a distal end of an electrode catheter into one of the one or more cardiac chambers of a patient; and calculating dipole densities d(y) by: a first receiver receiving mapping information from multiple electrodes located on one or more catheters, the mapping information received when the multiple electrodes are placed in the one or more cardiac chambers; a second receiver receiving anatomical information from at least one imaging instrument configured to produce a geometrical depiction of the one or more cardiac chambers; and a dipole density module generating the database of dipole densities d(y), wherein the dipole density module determines a dipole density for individual triangle shaped projections onto the cardiac chamber wall, where each triangle projection at a location y contributes ω(x,y) times the dipole density d(y) to a potential V(x) at a point x, wherein ω(x,y) is the solid angle for that triangle projection, and where: a) x represents a series of locations within one or more cardiac chambers; and b) V(x) is a measured potential at point x, said measured potential recorded by the multiple electrodes; and calculating distance or movement information by analyzing signals received from a sound sensor.

In various embodiments, the method can comprise calculating distance information comprises calculating tissue thickness information.

In various embodiments, the method can comprise using the dipole densities d(y) to locate an origin of abnormal electrical activity of a heart.

In various embodiments, wherein calculating the dipole densities can include a processor executing a computer program stored in a memory, the computer program embodying an algorithm for generating a table of dipole densities in the memory.

In accordance with another aspect of the invention, provided is a method for diagnosing tissue, said method comprising: placing a distal end of a catheter into one or more cardiac chambers of a patient; wherein the catheter comprises at least one electrode and at least one ultrasound element; determining a tissue movement via the at least one ultrasound element; determining an electrical charge via the at least one electrode; and determining tissue diagnostics based upon the tissue movement and the electrical charge.

In accordance with another aspect of the invention, provided is a medical method comprising: inserting a device of any of claim 1 through 122 into a delivery system; advancing the device through the delivery system and into a heart chamber; and steering the device and/or the delivery system such that the distal end of the device is positioned in approximately the geometric center of the heart chamber.

In accordance with another aspect of the invention, provided is a method of diagnosing tissue of a patient, comprising: combining electrical information and anatomical information; wherein the electrical information comprises information received from multiple electrodes constructed and arranged to record electrical signals produced by tissue; and wherein the anatomical information comprises information received by a sensor constructed and arranged to record sound signals.

In various embodiments, the electrical information indicative of adequate electrical activity and anatomical information indicative of adequate tissue motion can correlate to presence of healthy tissue.

In various embodiments, the electrical information indicative of adequate electrical activity and anatomical information indicative of inadequate tissue motion can correlate to presence of at least one of ischemic tissue or hibernating tissue.

In various embodiments, the electrical information can comprise signals larger than a threshold voltage.

In various embodiments, the electrical information indicative of inadequate electrical activity and anatomical information indicative of inadequate tissue motion can correlate to presence of scar tissue.

In various embodiments, the diagnosis can comprise an assessment of tissue ischemia.

In various embodiments, the diagnosis comprises an assessment of electrical integrity of cardiac cells.

In various embodiments, the diagnosis can further comprise an assessment of the functional status of the cardiac cells.

In various embodiments, the electrical information indicative of inadequate electrical activity and anatomical information indicative of inadequate tissue motion can correlate to presence of a complete ablation such as an ablation performed in a cardiac ablation performed to treat a cardiac arrhythmia.

In various embodiments, the complete ablation can comprise a transmural ablation.

In various embodiments, the electrical information can comprise dipole density information.

In various embodiments, the electrical information can comprise at least one of the following: depolarization, repolarization, speed of wavefront propagation, magnitude of voltage (max, min, gradient), timing of activation, and duration of activation.

In various embodiments, the method can further comprise ablating cardiac tissue by applying ablation energy for a time period.

In various embodiments, the anatomical information can comprise tissue thickness information and at least one of the ablation energy or the time period is adjusted based on the tissue thickness information.

In accordance with aspects of the present invention, provided is a method for performing a medical procedure on a patient, the method comprising: inserting a first catheter into the patient, wherein the first catheter comprises a first set of elements and at least one sensor; inserting a second catheter into the patient, wherein the second catheter comprises an elongate shaft and wherein the second catheter comprises a second set of elements; and attaching a clamp assembly to the second catheter, wherein the clamp assembly is constructed and arranged to be removably attached to the second catheter and to transmit vibrational energy.

In various embodiments, the first set of elements can comprise a sensor.

In various embodiments, the sensor can be selected from a group consisting of: temperature; pressure; electrical signal; electrode; sound; and combinations of these.

In various embodiments, the first set of elements can comprise a transducer.

In various embodiments, the transducer can be selected from the group consisting of: ablation element; electrode; sound; and combinations of these.

In various embodiments, the at least one sensor can comprise an ultrasound sensor.

In various embodiments, the at least one sensor can comprise a transducer.

In various embodiments, the transducer can comprise an ultrasound transducer.

In various embodiments, the second set of elements can comprise a sensor.

In various embodiments, the sensor can be selected from the group consisting of: temperature; pressure; electrical signal; electrode; sound; and combinations of these.

In various embodiments, the second set of elements can comprises a transducer.

In various embodiments, the transducer can be selected from a group consisting of: ablation element; electrode; sound; and combinations of these.

In various embodiments, the second catheter elongate shaft can comprise a proximal portion with a proximal end and a distal portion with a distal end.

In various embodiments, the clamp assembly can comprise a vibrational transducer configured to emit ultrasound waves.

In various embodiments, the clamp assembly can comprise a clamping mechanism constructed and arranged to be removably attached to the second catheter elongate shaft.

In various embodiments, the clamp assembly can be positioned on the proximal portion of the second catheter elongate shaft.

In various embodiments, the second catheter can comprise a handle.

In various embodiments, the clamp assembly can be positioned within 10 centimeters from the handle.

In various embodiments, the second catheter elongate shaft can further comprise a conduit constructed and arranged to transmit the ultrasound waves from the proximal portion to the distal portion of the second catheter elongate shaft.

In various embodiments, the clamp assembly can be positioned on the distal portion of the second catheter elongate shaft.

In various embodiments, the second catheter distal portion can be within 10 centimeters from the distal end of the second catheter elongate shaft.

In various embodiments, the second catheter elongate shaft can further comprise multiple electrodes wherein the multiple electrodes are positioned on the distal end of the second catheter elongate shaft and the clamp assembly is constructed and arranged to vibrate the multiple electrodes.

In various embodiments, the multiple electrodes can comprise the multiple electrodes described above.

In various embodiments, the second catheter elongate shaft can further comprise at least one thermocouple positioned on the second catheter elongate shaft wherein the clamp assembly is constructed and arranged to vibrate the at least one thermocouple.

In various embodiments, the second catheter elongate shaft can further comprise at least one support arm attached to the second catheter elongate shaft wherein the clamp assembly is constructed and arranged to vibrate the at least one support arm.

In various embodiments, the at least one support arm can comprise at least one of a sensor or a transducer.

In various embodiments, the second catheter elongate shaft can further comprise at least one ablation element attached to the second catheter elongate shaft wherein the clamp assembly can be constructed and arranged to vibrate the at least one ablation element.

In various embodiments, the second catheter elongate shaft can further comprise at least one sensor attached to the second catheter elongate shaft wherein the clamp assembly can be constructed and arranged to vibrate the at least one sensor where the sensor is selected from the group consisting of: temperature; pressure; electrical signal; electrode; sound; and combinations of these.

In various embodiments, the second catheter elongate shaft can further comprise at least one transducer attached to the second catheter elongate shaft wherein the clamp assembly can be constructed and arranged to vibrate the at least one transducer where the transducer is selected from the group consisting of: ablation element; electrode; sound; and combinations of these.

In various embodiments, the second catheter elongate shaft can further comprise at least one ultrasound crystal positioned on the second catheter elongate shaft wherein the clamp assembly can be constructed and arranged to vibrate the at least one crystal.

In various embodiments, the clamp assembly can be constructed and arranged to vibrate the second catheter elongate shaft.

In various embodiments, the clamp assembly can be positioned such that the clamp assembly can be located outside the patient's body while the distal end of the second catheter elongate shaft is located within the patient's body.

Provided is device, system, and/or method for real time, non-contact imaging and distance measurements using ultrasound for dipole density mapping, as well as methods for diagnosing tissue health, as depicted in the drawings included herein.

BRIEF DESCRIPTION OF THE DRAWINGS

The accompanying drawings, which are incorporated in and constitute a part of this specification, illustrate various embodiments in accordance with the present invention, and together with the description, serve to explain the principles of the inventions.

DETAILED DESCRIPTION

Figure 1:
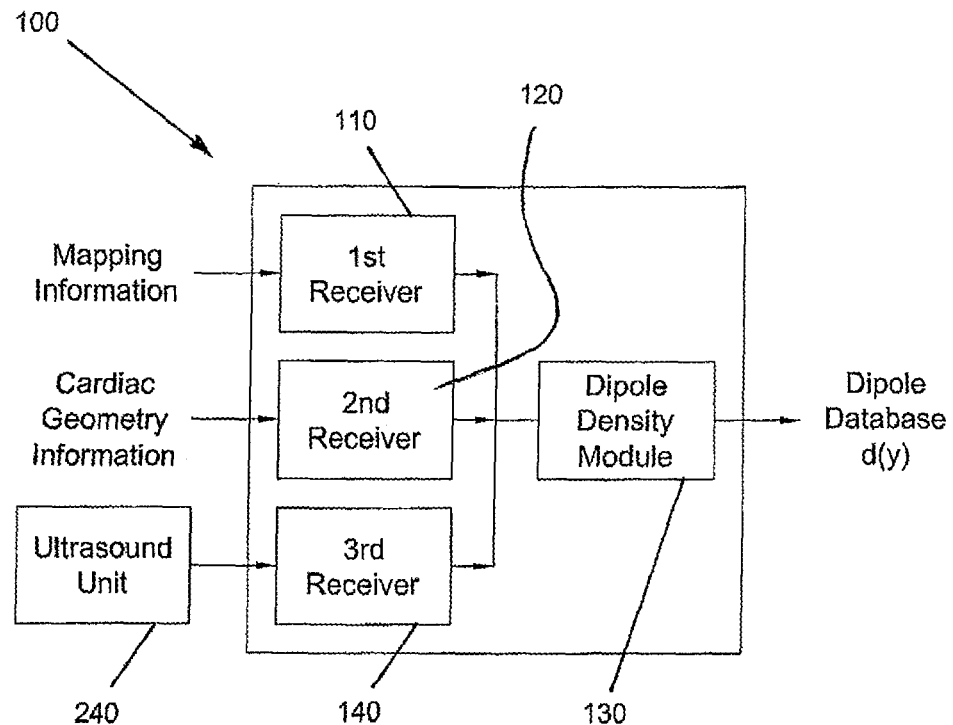
FIG. 1 illustrates a schematic view of an embodiment of a device for determining a database table of dipole densities d(y) of at least one heart chamber, consistent with aspects of the present invention.

A device for calculating surface charge densities has been described in detail in PCT International Application Number PCT/CH2007/000380 (hereinafter the '380 patent application), filed Aug. 3, 2007, and entitled METHOD AND DEVICE FOR DETERMINING AND PRESENTING SURFACE CHARGE AND DIPOLE DENSITIES ON CARDIAC WALLS.

As discussed in the '380 patent application, research indicated that the use of the surface charge densities (i.e. their distribution) or dipole densities (i.e. their distribution) to generate distribution map(s) would lead to more detailed and precise information on electric ionic activity of local cardiac cells than potentials. Surface charge density or dipole densities represent precise and sharp information of the electric activity with a good spatial resolution, whereas potentials resulting from integration of charge densities provide only a diffuse picture of electric activity. The electric nature of cardiac cell membranes comprising ionic charges of proteins and soluble ions can be precisely described by surface charge and dipole densities. The surface charge densities or dipole densities cannot be directly measured in the heart, but instead must be mathematically and accurately calculated starting from measured potentials. In other words, the information of voltage maps obtained by current mapping systems can be greatly refined when calculating surface charge densities or dipole densities from these.

The surface charge density means surface charge (Coulombs) per unit area (cm$^2$). A dipole, as such, is a neutral element, wherein a part comprises a positive charge and the other part comprises the same but negative charge. A dipole might represent the electric nature of cellular membranes better, because in biological environment ion charges are not macroscopically separated.

In order to generate a map of surface charge densities (surface charge density distribution) according to the '380 patent application, the geometry of the given heart chamber must be known. The 3D geometry of the cardiac chamber is typically assessed by currently available and common mapping systems (so-called locator systems) or, alternatively, by integrating anatomical data from CT/MRI scans. For the measurement of potentials the non-contact mapping method a probe electrode was used. The probe electrode may be a multi-electrode array with elliptic or spherical shape. The spherical shape has certain advantages for the subsequent data analysis. But also other types or even several independent electrodes could be used to measure $V_e$. For example, when considering the ventricular cavity within the endocardium and taking a probe electrode with a surface $S_p$, which is located in the blood, it is possible to measure the potential $V(x,y,z)$ at point x,y,z on the surface $S_p$. In order to calculate the potential at the endocardial surface $S_e$ the Laplace equation:

$$\Delta V = \left(\frac{\partial^2}{\partial x^2} + \frac{\partial^2}{\partial y^2} + \frac{\partial^2}{\partial z^2}\right)V = 0 \tag{1}$$

needs to be solved, wherein V is the potential and x,y,z denote the three dimensional coordinates. The boundary conditions for this equation are $V(x,y,z)=V_p(x,y,z)$ on $S_p$, wherein $V_p$ is the potential on surface of the probe.

The solution is an integral that allows for calculating the potential V(x'y'z') at any point x'y'z' in the whole volume of the heart chamber that is filled with blood. For calculating said integral numerically a discretisation of the cardiac surface is necessary and the so called boundary element method (BEM) has to be used.

The boundary element method is a numerical computational method for solving linear integral equations (i.e. in surface integral form). The method was applied in many areas of engineering and science including fluid mechanics, acoustics, electromagnetics, and fracture mechanics.

The boundary element method is often more efficient than other methods, including the finite element method. Boundary element formulations typically give rise to fully populated matrices after discretisation. This means, that the storage requirements and computational time will tend to grow according to the square of the problem size. By contrast, finite element matrices are typically banded (elements are only locally connected) and the storage requirements for the system matrices typically grow quite linearly with the problem size.

With the above in mind, all potentials $V_p$ (x1'y1'z1') on the surface of the probe can be measured. To calculate the potential $V_e$ on the wall of the heart chamber, the known geometry of the surface of the heart chamber must be divided in discrete parts to use the boundary element method. The endocardial potentials $V_3$ are then given by a linear matrix transformation T from the probe potentials $V_p$: $V_e=T\ V_p$.

After measuring and calculating one or more electric potential(s) $V_e$ of cardiac cells in one or more position(s) P(x,y,z) of the at least one given heart chamber at a given time t. The surface charge density and the dipole density are related to potential according to the following two Poisson equations:

$$\Delta V_e = \rho(P)\delta_{S_e}(P) \tag{2}$$

$$\Delta V_e = \frac{\delta}{\partial n}(v\delta_{S_e}(P)) \tag{3}$$

wherein $\rho(P)$ is the surface charge density in position P=x,y,z, $\delta_{S_e}(P)$ is the delta-distribution concentrated on the surface of the heart chamber $S_e$ and v is the dipole density.

There is a well known relationship between the potential $V_e$ on the surface of the wall of the heart chamber and the surface charge (4) or dipole densities (5).

$$V_e(P) = -\frac{1}{4\pi}\int_{S_e}\frac{\rho(P')}{|P'-P|}d\sigma(P') \tag{4}$$

$$V_e(P) = \frac{1}{4\pi}\int_{S_e}v(P')\frac{\partial}{\partial n_{P'}}\frac{1}{|P-P'|}d\sigma(P') \tag{5}$$

(For a review see Jackson J D. Classical Electrodynamics, 2n$^d$ edition, Wiley, New York 1975.)

The boundary element method again provides a code for transforming the potential $V_e$ in formulas 4 and 5 into the desired surface charge densities and dipole densities, which can be recorded in the database.

In another embodiment of the method, the electric potential(s) $V_4$ is (are) determined by contact mapping. In this case the steps for calculating the electric potential $V_e$ are not necessary, because the direct contact of the electrode to the wall of the heart chamber already provides the electric potential $V_e$.

In a preferred embodiment, the probe electrode comprises a shape that allows for calculating precisely the electric potential $V_e$ and, thus, simplifies the calculations for transforming $V_e$ into the desired charge or dipole densities. This preferred geometry of the electrode is essentially ellipsoidal or spherical.

In order to employ the method for determining a database table of surface charge densities of at least one given heart chamber in the context of the '380 patent application, it was preferred to use a system comprising at least:
 a) one unit for measuring and recording electric potentials V at a given position P(x,y,z) on the surface of a given heart chamber (Contact mapping) or a probe electrode positioned within the heart, but without direct wall contact (noncontact mapping)
 b) one A/D-converter for converting the measured electric potentials into digital data,
 c) one memory to save the measured and/or transformed data, and
 d) one processor unit for transforming the digital data into digital surface charge density or dipole density data.

It is noted that numerous devices for localising and determining electric potentials of cardiac cells in a given heart chamber by invasive and non-invasive methods are well known in the art and have been employed by medical practitioners over many years. Hence, the method, system, and devices of the '380 patent application did not require any particular new electrodes for implementing the best mode for practicing the invention. Instead, the '380 patent application provided a new and advantageous processing of the available data that will allow for an increase in precision, accuracy and spatial resolution of cardiac activation mapping when compared to prior art systems based on electric surface potentials in the heart only. The systems and methods of the '380 patent application would also allow for providing superior diagnostic means for diagnosing cardiac arrhythmias and electric status of heart cells including metabolic and functional information.

The present invention provides an improved device, system and method for calculating and visualizing the distribution and activity of dipole charge densities on a cardiac wall. The dipole densities are directly determined geometrically, avoiding the errors encountered using previous extrapolation algorithms In one embodiment, the device of the present invention comprises multiple electrodes located on one or more catheters, a transducer, and a sensor. The device may be used to create a three dimensional database of dipole densities d(y) and distance measurements at the surface of one or more cardiac chambers of a patient. The distance measurements may include but are not limited to: the distance between at least one of the multiple electrodes and the heart wall, the distance between at least one of the multiple electrodes and the transducer and/or sensor, and the distance between the heart wall and the transducer and/or sensor. The distance measurements may be calculated by analyzing the sensor recorded angle and/or the sensor frequency changes. The device may also be configured to produce continuous, real time images of the tissue of a patient. Examples of images may include, but are not limited to: one more cardiac chambers, a cardiac wall, the tissue proximate at least one of the multiple electrodes, at least one of the multiple electrodes, and combinations of these. The device may provide one or more of: tissue image information such as tissue position, tissue thickness (e.g. cardiac wall thickness) and tissue motion (e.g. cardiac wall motion) information; distance information such as distance between two tissue locations, distance between a tissue location and a device component location, and distance between two device component locations; tissue electrical activity information; status of ablation of a portion of tissue; and combinations of these.

The present invention incorporates a transducer and a sensor, each preferably ultrasonic and contained in a single component. The transducer and sensor are configured to determine a non-contact measurement of the distance or presence of one or more targets such as tissue of a patient or a component of one or more catheters or other devices. Information is produced by transmitting an ultrasound wave followed by measuring the time required for the sound echo to return to and be sensed by the sensor, thus determining the distance between all reflected surfaces and the sensor/transmitter. This additional information enables a more precise dipole density d(y) measurement. Measurements may be taken to determine the thickness of an object, such as the thickness of cardiac tissue, which may be used to determine an ablation parameter such as power or time of energy delivery.

Utilizing the present invention, a method for diagnosing tissue is also disclosed. Analyzing the information gathered from a catheter device, specifically the tissue movement and the tissue's electrical charge, a clinician is able to determine the health of the tissue. For example, if adequate tissue movement has been detected, and the tissue produces an electrical signal indicative of a healthy state, then the tissue is determined to be healthy. With the tissue diagnosis, a clinician may determine what type of treatment, e.g. ablation, is favorable to the patient.

In accordance with the present invention, provided is a device that measures and calculates a database of dipole densities d(y) on the cardiac wall. The actual measured potentials in the heart result from electrical activity of cells, which can be regarded as dipoles. The dipoles consist of ion charges on both sides of biological membranes. The use of dipole densities offers a precise representation of the electrical activity. Systems and methods in accordance with the present invention efficiently and effectively calculate the dipole densities utilizing one or more mathematical theorems. This calculation is significantly more precise than calculations of virtual potentials produced by current systems, which lose spatial precision because of the required numerical methods and the use of potentials instead of dipole densities. Systems and methods in accordance with the present invention are efficient in calculating dipole densities geometrically, such as through the use of computer systems, or similar microcontroller and/or mathematical processing equipment.

Definitions. To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited to, individuals requiring medical assistance, and in particular, patients with an arrhythmia such as atrial fibrillation (AF).

As used herein, in the illustrative embodiments, the term "solid angle" is the two-dimensional angle subtended in the three dimensional space between a triangle on the heart wall and the position x of observation. When viewed from location x, straight lines are drawn from point x to the vertices of the triangle, and a sphere is constructed of radius r=1 with center of x. The straight lines then define a triangular section on the surface of the unit sphere. The solid angle is equal to the surface area of that triangle. As used herein, in the illustrative embodiments, the term "dipole density" refers to a three dimensional table of density magnitudes and d(y) generally refers to three dimensional system or space.

The methods and devices of the present invention have advantages over previous prior art devices. FIGS. 1-6 illustrate various preferred embodiments of devices, systems and methods in accordance with aspects of the present invention. However, the present invention is not limited to these particular configurations.

Referring now to FIG. 1, a schematic view of an embodiment of a device for determining a database table of dipole densities of at least one heart chamber of a patient is illustrated. Device 100 includes a first receiver 110 configured to receive electrical potentials from a separate device, such as a device including a multi-electrode mapping catheter placed in the circulating blood within a chamber of the patient's heart. Device 100 further includes a second receiver 120 configured to receive cardiac geometry information (e.g. the geometric contour of the cardiac chamber wall), such as from an instrument including, but not limited to: Computed Tomography; MRI; Ultrasound; a multi-electrode mapping catheter; and combinations of these. Alternatively, a standard geometry can be loaded representing a model of the cardiac chamber.

Device 100 further comprises a third receiver 140 configured receive ultrasound information from ultrasound unit 240. Ultrasound unit 240 comprises a transducer and sensor. In a preferred embodiment, the transducer comprises an ultrasound transducer configured to produce high frequency vibrations, i.e., ultrasound waves, in a pulsed or constant manner Typically, the ultrasound transducer produces sound waves having a wavelength of 5-15 MHz. In some embodiments, the transducer and the sensor are a single component such as a piezo crystal configured to both transmit and sense ultrasound signals.

In this embodiment, the sensor is preferably an ultrasound sensor configured to record or otherwise detect the emitted ultrasound waves from the ultrasound transducer. The sensor may be further configured to determine real-time continuous measurements of the position of at least one of the multiple electrodes and/or the sensor within the cardiac chamber. Knowing the speed of sound in the particular environment, as well as the timing of the delivery of sound waves by the transducer, the distance between the sensor, transducer and one or more reflected surfaces can be calculated.

In a typical embodiment, a piezo crystal transmits ultrasound waves and receives the reflections of those waves. As is well known to those of skill in the art, the timing between transmitting and receiving can be used to determine locations of the reflective surfaces such as tissue surfaces and device component surfaces. In one embodiment, precise locations and measurements of target cardiac tissue is determined, resulting in a more precise and effective therapy. The ultrasound crystal will transmit a signal that is reflected off of tissue surfaces, which can be used to determine the distance from the mapping electrode to the tissue. This distance will be fed into the software algorithm to aid in the calculation of electrical activity via dipole density or direct electrical signal analysis.

By having the precise distance, the overall calculations will be very precise (frequency; it is approximately 3 megahertz and may be up to the 18 megahertz). The emitted waves may be at constant frequency or produced by a chip of changing frequency (to allow pulse compression on reception). The precision in dipole density calculations along with the distance measurement will allow for the precise detailing of the cardiac cells in the electrical activity and will allow for the precise identification of cell activity to identify which cells are the earliest sites of activation. In one embodiment, the sensor may be configured to automatically detect the distance from the sensor to the cardiac wall via a first reflection and detect the wall thickness via a second reflection. Other distances measurements include, but are not limited to: the distance between at least one of the multiple electrodes and the heart wall, the distance between at least one of the multiple electrodes and the transducer and/or sensor, and the distance between the heart wall and the transducer and/or sensor. In another embodiment, the ultrasonic element integrates multiple reflections to construct a complete image including wall distance and thickness. In yet another embodiment, the ultrasonic element provides information relative to the positioning of the cardiac tissue and one or more electrodes, such as to localize an ablation and/or a mapping catheter including those one or more electrodes.

In one embodiment, the sensor and/or transducer includes at least one crystal, typically comprised of a piezoelectric material, which is positioned proximate to the center of each electrode within an electrode array. In another embodiment, the crystal is positioned between two or more electrodes, such as to create a device with a ratio of mapping electrodes to crystals of 1:1, 2:1, 5:2, 3:1, 4:1 or another ratio. The at least one crystal may be constructed and arranged to receive the signals transmitted by an ultrasound transducer, and/or the reflections of those signals. The at least one crystal may be in a fixed position or may be rotated via a rotating mechanism such as by a rotating shaft operably attached to the at least one ultrasound crystal. The rotation may be a full rotation, e.g. 360°, such that the full circumference of the cardiac chamber is measured. Alternatively, the rotation of the at least one crystal may be partial. Alternatively or additionally, one or more ultrasound crystals may be moved axially, such as in a reciprocating motion to produce an image of an increased length and/or to produce a 3-D reconstructed image. In another embodiment, the sensor and/or transducer comprise a plurality of crystals arranged in an array, for example, a circumferential array.

In another embodiment, the ultrasound sensor and/or transducer may comprise a probe operably attached to the catheter and configured to vibrate one or more catheter components. In an alternate embodiment, the ultrasound sensor and/or transducer comprise a piezoelectric film covering each electrode within the array. In yet another embodiment, the ultrasound sensor and/or transducer comprise a piezoelectric cable operably connected to each electrode.

The ultrasound sensor and/or transducer may be housed within a mechanical clamping assembly which may be attached to the shaft of a catheter, such as a mapping catheter or an ablation catheter. Additionally, a particular clamping assembly with a particular ultrasound frequency may be used with a particular catheter, while a second clamping assembly with a second ultrasound frequency may be used with a second catheter. In another embodiment, the ultrasound sensor and/or transducer may be directly inserted into the mapping catheter.

In yet another embodiment, the device may comprise a multiple arm assembly such that the sensor and/or transducer are mounted to the multiple arm assembly. Additionally, at least one electrode may be mounted to the multiple arm assembly. In an alternate embodiment, the sensor and/or transducer may be constructed as part of the electrode. For example, the device may comprise a sensor/electrode combination. In another embodiment, the sensor and/or transducer may be constructed as a forward facing sensor and arranged to project a signal directly in line with an electrode to the tissue. In yet another embodiment, the sensor and/or transducer may be configured to be rotated such that the sensor and/or transducer is facing each electrode individually, and a signal may be emitted past each electrode.

In some embodiments, the device is constructed and arranged to be steered such that the distal end of the device is positioned in approximately the geometric center of the heart chamber of a patient. In this embodiment, the catheter may be loaded into a delivery system, e.g., a delivery sheath and may be advanced from the delivery sheath such that the dipole density mapping system comprising the ultrasound sensor is located in the blood and the heart chamber. Also in this embodiment, the delivery sheath may comprise a central lumen configured to slidingly receive an ablation catheter. This configuration of the device may allow a user to perform a diagnostic procedure with one device. Additionally, only one trans-septal crossing may be necessary. In yet another embodiment, the device may be steerable. For example, a user may determine the ablation site via real-time tissue analysis and imaging, and subsequently the device may be steered to the desired location. Steering of the device may be achieved via cables which may be housed in a lumen of a delivery sheath similar to the delivery sheath described above.

Device 100 further includes a dipole density module 130 which comprises mathematical processing element, such as a computer or other electronic module including software and/or hardware for performing mathematical or other calculations. Dipole density module 130 receives mapping information from first receiver 110 and cardiac geometry information from second receiver 120. Dipole density module 130 preferably uses one or more algorithms to process the received mapping and geometry information to produce a database table of dipole densities, e.g., a three dimensional database table of dipole densities.

The geometrical model of the cardiac chamber is processed by dipole density module 130 into multiple small triangles (triangularization). When the triangles are sufficiently small, the dipole density at each triangle can be regarded as constant. In a preferred embodiment, a standard cardiac chamber of 4-6 cm diameter is divided up into over 1000 triangles. In another preferred embodiment, the number of triangles determined by dipole density module 130 is based on the size of the heart chamber. With the electrodes positioned in a cardiac chamber by a clinician, such as an electrophysiologist, the potentials at each electrode are recorded. Each triangle is seen by the corresponding electrode under a certain solid angle. The dipole density module 130 computes the solid angle $\omega(x,y)$ subtended by each triangle at position y on each electrode at position x on the multi-electrode catheter. If the dipole density at the triangle is d(y), the triangle contributes $\omega(x,y)$ times d(y) to the potential V(x) at the position x on the multi-electrode catheter. The total measured potential V(x) is the sum resulting from all the triangles. A detailed description is provided in reference to FIG. 3 herebelow.

In a preferred embodiment, dipole density module 130 implements a progressive algorithm that can be modified and/or refined in order to improve spatial and/or time resolution of the database of dipole densities that are produced. The dipole densities d(y) are obtained by solving a linear system of equations. This calculation requires some care to avoid numerical instabilities. Thereby a map of dipole densities can be created at each corresponding time interval. The synthesis of the maps generates a cascade of the activation sequence of each corresponding heart beat that can be used to define the origin of the electrical activity, arrhythmias or diagnose cardiac disease.

The measuring electrodes used in the present invention are placed in the blood flow in a heart chamber, a relatively homogeneous condition, such that the mathematical analysis of the present invention is well applicable. In a preferred embodiment, skin electrodes are also implemented such that dipole density module 130 can use the information received from the skin electrodes to calculate and/or recalculate the dipole densities for the cardiac wall. The spatial resolution which can be obtained by invasive (i.e., placed in the heart chamber) multi-electrode potential measurements is limited by the number of electrodes that can be placed in any cardiac chamber, such as the Left Atrium (LA). Skin placed electrodes, such as electrodes placed on the thorax, are not as space limited. However, due mainly to the inhomogeneous structure of the body, it is difficult to localize the actual sources of the skin electrode measured potentials. A highly complicated boundary value problem must be solved with boundary conditions that are poorly known, and previous attempts at determining the "action potential" from body surface ECG (alone) have not been very successful.

The badly defined boundary value problem can be avoided by an additional measurement (in addition to the skin electrode measurements) of the multi-electrode array of the present invention. A small sinusoidal voltage $V_l$ is applied to each electrode l=1, ... L on the electrode array in the heart, and the resulting voltages $W_k$, k=1, .... K is measured at the surface electrodes. This yields the KXL transition matrix $A_{kl}$ $$W_k = \sum_{l=1}^{L} A_{kl} V_l \tag{6}$$

Calculating solid angles produces the linear transformation $B_{ln}$ between the electrode array potentials $V_l$ and the dipole densities $d_n$, n=1, ... N of N regions of the heart wall:

$$V_l = \sum_{n=1}^{N} D_{ln} d_n \tag{7}$$

N is chosen to be N=K+L where K is the number of surface electrodes and L is the number of internally placed array electrodes. Substituting equation (7) into (6) we have:

$$W_k = \sum_{l=1}^{L} \sum_{n=1}^{N} A_{kl} B_{ln} d_n \tag{8}$$

Therefore, by simultaneous measuring of the potentials of the cardiac activity with all K+L electrodes, N=K+L dipole densities of N regions on the heart wall can be calculated. This method yields a higher spatial resolution than the L array electrodes alone. In the solution of the linear system of equations (7)+(8), regularization techniques must be used (e.g. Tikhonov regularization and its modifications) in order to avoid numerical instabilities.

Figure 2:
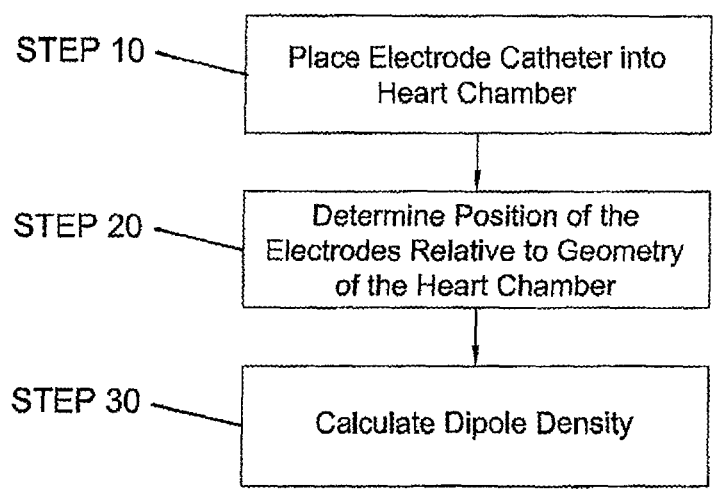
FIG. 2 illustrates a flow chart of an embodiment of a preferred method for determining a database table of dipole densities of at least one heart chamber, consistent with aspects of the present invention.

Referring now to FIG. 2, an embodiment of a preferred method for determining a database table of dipole densities of at least one heart chamber of a patient is illustrated. In Step 10, a multi-electrode array is placed within the corresponding heart chamber. In Step 20, the geometry of the corresponding heart chamber may be obtained in relation to the multi-electrode array position via an ultrasound transducer and sensor, typically a single ultrasound crystal configured to both emit and record ultrasound signals. In addition to chamber geometry, magnitude and other properties of wall motion of cardiac wall tissue can be determined. For example, an ultrasound transducer positioned on a distal portion of the catheter is configured to transmit ultrasound waves to the wall of the cardiac chamber as well as to components of one or more devices within the cardiac chamber. In an alternative embodiment, an ultrasound transducer is attached to a proximal portion of a catheter shaft and configured to vibrate the shaft or one or more components mounted to the shaft, thus sending ultrasound waves to the wall of the cardiac chamber. One or more ultrasound sensors detect reflections of the transmitted ultrasound. In addition, the thickness of a patient's tissue as well as the motion of the tissue may be determined, such as to enable a clinician to determine what treatment, (e.g., what ablation parameters) is appropriate for a patient. A detailed description of one embodiment of the ultrasound transducer and sensor that can be utilized in this step is described in FIG. 1 hereabove. Alternatively or additionally, the geometry of the corresponding heart chamber is obtained in relation to the multi-electrode array position, such as by moving around a second mapping electrode or by importing a geometry model from an imaging study (e.g., using computed tomography, MRI or ultrasound before or after the multi-electrode array of electrodes has been placed in the heart chamber). The surface of the geometry of the corresponding heart chamber is divided into small triangles, typically at least 1000 small triangles.

In Step 30, the dipole density d(y) can be calculated from the measured potential values and the calculated solid angles. The measurements can be repeated successively during the cardiac cycle giving a high time-resolution during each millisecond. The information of the timely dependent dipole densities can be depicted as an activation map of the corresponding heart chamber for the given heart beat. The information can be used to diagnose and/or treat a patient with a cardiac arrhythmia, such as atrial fibrillation.

In a preferred embodiment, the information is used to determine cardiac wall treatment locations for lesion creation, such as a lesion created in the Left or Right atrium, by an RF, ultrasound or cryogenic ablation catheter. In another preferred embodiment, the multiple electrode mapping array is placed in a ventricle and the dipole densities are determined for the ventricular wall, such as to detect ischemia or quantify myocardial function.

In one embodiment, the device includes one or more catheters constructed and arranged to be steered such that the distal end of the catheter can be positioned in approximately the geometric center of the heart chamber of a patient. In this method, a mapping catheter may be loaded into a delivery system (e.g. a delivery sheath) and may be advanced from the delivery system such that the dipole density mapping system comprising an ultrasound sensor and transducer is located in the circulating blood of the heart chamber.

Figure 3:
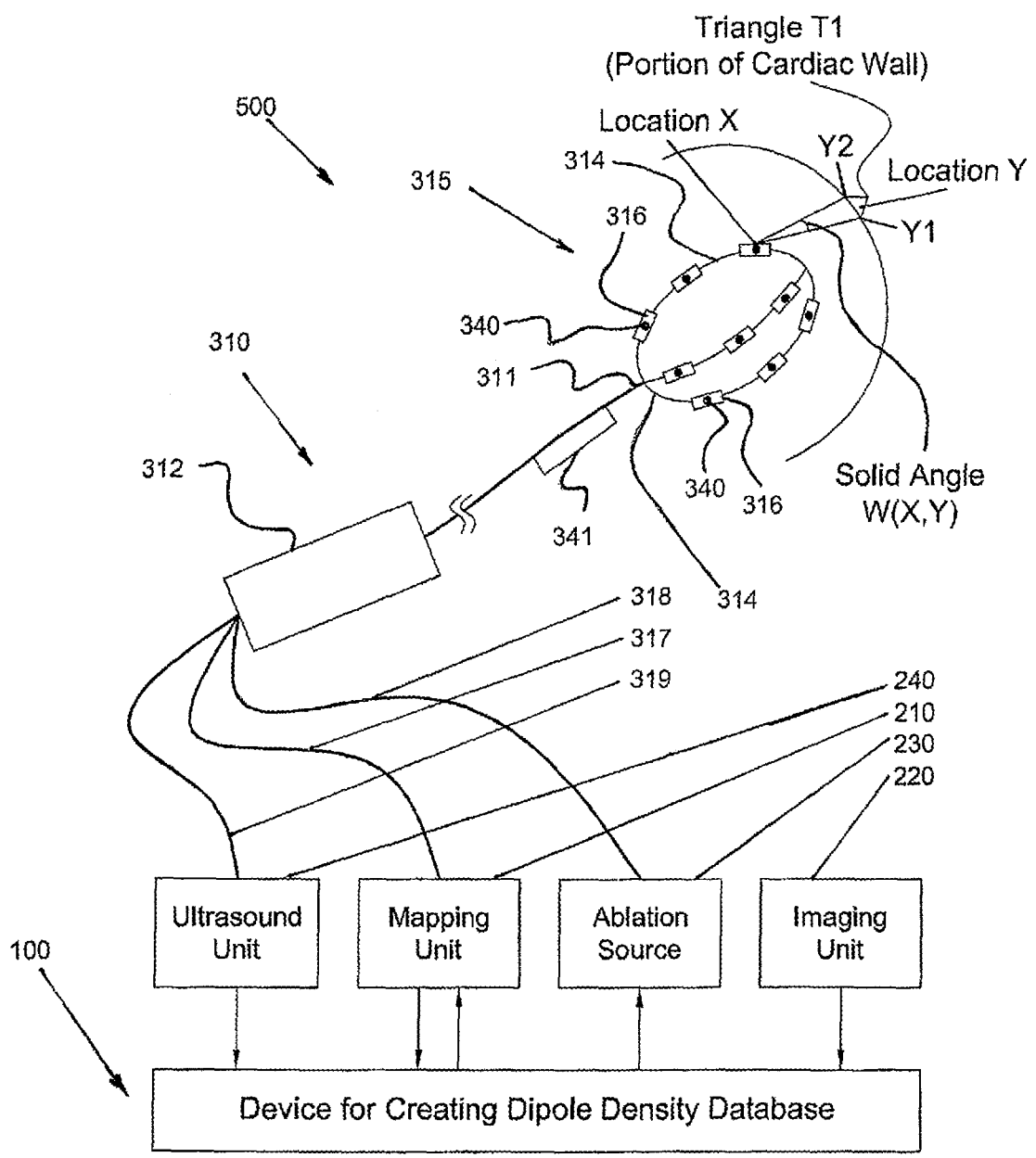
FIG. 3 illustrates a schematic view of an embodiment of a system for determining a database table of dipole densities of at least one heart chamber with help of the solid angle ω(x,y) consistent with aspects of the present invention.

Referring now to FIG. 3, an embodiment of a system for determining a database table of dipole densities of at least one heart chamber of a patient is illustrated. System 500 includes device 100, which is configured to create a database table of three dimensional dipole densities d(y) based on voltage potential measurements within the heart chamber and image information relating to the heart chamber, as has been described hereabove. System 500 further includes imaging unit 220, which is configured to provide a two or three-dimensional image of the heart chamber to device 100. Imaging unit 220 may perform at least one of Computed Tomography, MRI and/or ultrasound imaging. Imaging unit 220 may produce any form of real or virtual models of the cardiac chambers, such that a triangularization analysis is possible.

System 500 further includes mapping catheter 310, which includes shaft 311, shown inserted into a chamber of a patient's heart, such as the Left Atrium (LA). At the distal end of shaft 311 is an electrode array 315 including multiple electrodes 316. Electrode array 315 is shown in a basket construction, comprising support arms 314, but numerous other constructions can be used including multiple independent arms, spiral arrays, electrode covered balloons, and other constructions configured to place multiple electrodes into a three-dimensional space. In a preferred embodiment, any catheter with a three-dimensional array of electrodes can be used to supply the mapping information to device 100.

In this embodiment, electrodes 316 are connected to wires, not shown, but traveling proximally to cable 317, which is electrically connected to a mapping unit 210, such as an electrocardiogram (ECG) unit. Mapping unit 210 includes a monitor for displaying information, such as the potentials recorded by electrodes 316, as well as the dipole density information produced by device 100. In an alternative embodiment, device 100 further includes a monitor, not shown, but configured to display one or more of: dipole density information; potentials recorded by electrodes 316; and cardiac chamber contours and other geometry information. In a preferred embodiment, dipole density and or recorded potentials information is shown in reference to a three-dimensional representation of the heart chamber into which catheter 310 is inserted. In an alternative embodiment, imaging unit 220 may include a device configured to create an image of the cardiac chamber from signals recorded from an electrode catheter, such as catheter 310.

System 500 may include a device for treating a cardiac arrhythmia, such as ablation source 230, which is electrically attached to electrodes 316 via cable 318. Alternatively or additionally, ablation source 230 can be attached to a different ablation catheter, such as a single or multiple ablation element catheter configured to deliver ablation energy such as RF energy, cryogenic energy, or other tissue disrupting energy.

System 500 may further comprise ultrasound unit 240, which is operably connected to ultrasound sensor, crystal 340 via cable 319. Unit 240 includes ultrasound transducer 341, an operably attachable clamping assembly configured to be placed around the shaft of a catheter device and cause one or more components of the catheter device to transmit ultrasound waves, such as waves configured to reflect off one or more structures and be recorded by crystal 340. Unit 240 processes the measurement data obtained by crystal 340 (i.e. the reflections recorded by crystal 340) and forwards the data to device 100. Measurement data may include the position of crystal 340 relative to the cardiac chamber and the electrodes 316, as has been described in detail in reference to FIG. 1 hereabove.

As shown in FIG. 3, triangle T1, defined by device 100 is at location Y. Electrode 316a of catheter 310 is at location X. The geometric relationship between triangle T1 and Location X is defined by the solid angle, angle $\acute{\omega}(X,Y)$. Device 100 includes dipole density module 130, as shown in FIG. 1, such that each triangle at location y contributes $\acute{\omega}(x,y)$ times the dipole density d(y) to the potential V(x) at the position x on a multi-electrode. Solid angle $\acute{\omega}(x,y)$, as defined above, corresponds to the triangle at a location y and the electrode at positions x on the multi-electrode array. The dipole density module 130, as shown in FIG. 1, of device 100 determines from the total measured potential V(x), which is the sum resulting from all the triangles defined by device 100, the desired dipole density d(y).

When sufficient potentials values V(x) are measured (e.g. from 10 to 10,000 with increasing number of measured potentials providing more accurate results), the dipole density d(y) at many equally distributed regions y on the cardiac wall is calculated by solving a linear equation system. By interpolation of the measured potentials (e.g. with help of splines) their number can be increased to a higher number of regions. The solid angle $\acute{\omega}(x,y)$ of a region is the sum of the solid angles of the individual triangles in the region on the cardiac wall. This calculation of dipole density results, such as via an automatic computer program forming at least part of dipole density module 130, as shown in FIG. 1.

In a preferred embodiment, the results are presented in a visual, anatomical format, such as depicting the dipole densities on a geometric image of the cardiac wall in relation to time (t). This format allows a clinician, such as an electrophysiologist, to determine the activation sequence, or other electrical and mechanical measures, on the cardiac wall, such as to determine treatment locations for a cardiac arrhythmia or other inadequacy in cardiac tissue health, such as force of tissue contraction and motion of the chamber wall. The results may be shown on a display of mapping unit 210, or on a separate unit such as a display included with device 100, display not shown but preferably a color monitor. In a preferred embodiment, the device of the present invention is implemented as, or includes, a software program that is executable by at least one processor. The software program can be integrated into one or more of: an ECG system; a cardiac tissue ablation system; an imaging system; a computer; and combinations of these.

In a preferred embodiment, the multi-electrode catheter includes at least ten electrodes, configured to represent a three dimensional body with known geometry. The electrodes are preferably positioned in a spherical geometry, such as a spherical geometry created in a basket catheter, comprising support arms 314. Elliptical electrode array geometries may be used, such as those provided in the Ensite Array Catheter, manufactured by St. Jude Medical of St. Paul Minn. In an alternative embodiment, multiple catheters are inserted into the heart chamber to provide the multiple electrodes.

In an alternative embodiment, the electrodes of the multi-electrode mapping array are repositioned during the method of determining dipole densities. Repositioning of electrodes can be beneficial to increase the number of measured potential values, if electrode positions are known. Therefore, repositioning is in concordance with adjustment of the geometry map in relation to the multi-electrode mapping catheter.

Figure 4:
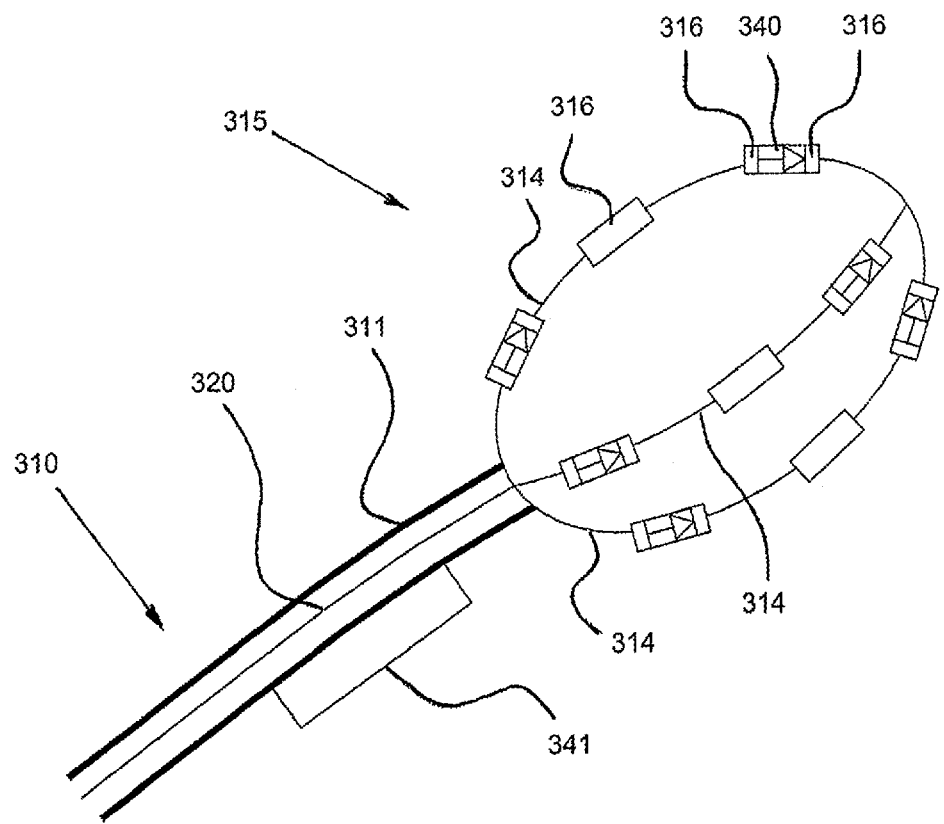
FIG. 4 illustrates a side view of an end portion of a catheter comprising ultrasound elements attached to multiple support arms, consistent with aspects of the present invention.

Referring now to FIG. 4, a side view of a catheter comprising an ultrasound sensor configured to determine real-time continuous measurements of the position of the catheter within a cardiac chamber is illustrated. Catheter 310 comprises shaft 311 and array 315 positioned on the distal end of shaft 311. Array 315 comprises multiple support arms 314 which include one or more electrodes 316 and one or more sensors, ultrasound crystal 340. Each crystal 340 may be positioned on electrode 316, on a support arm of array 315, or at another catheter 310 location. In a preferred embodiment, crystal 340 is located between two electrodes 316 as shown, or in a center portion a single electrode 316.

Figure 5:
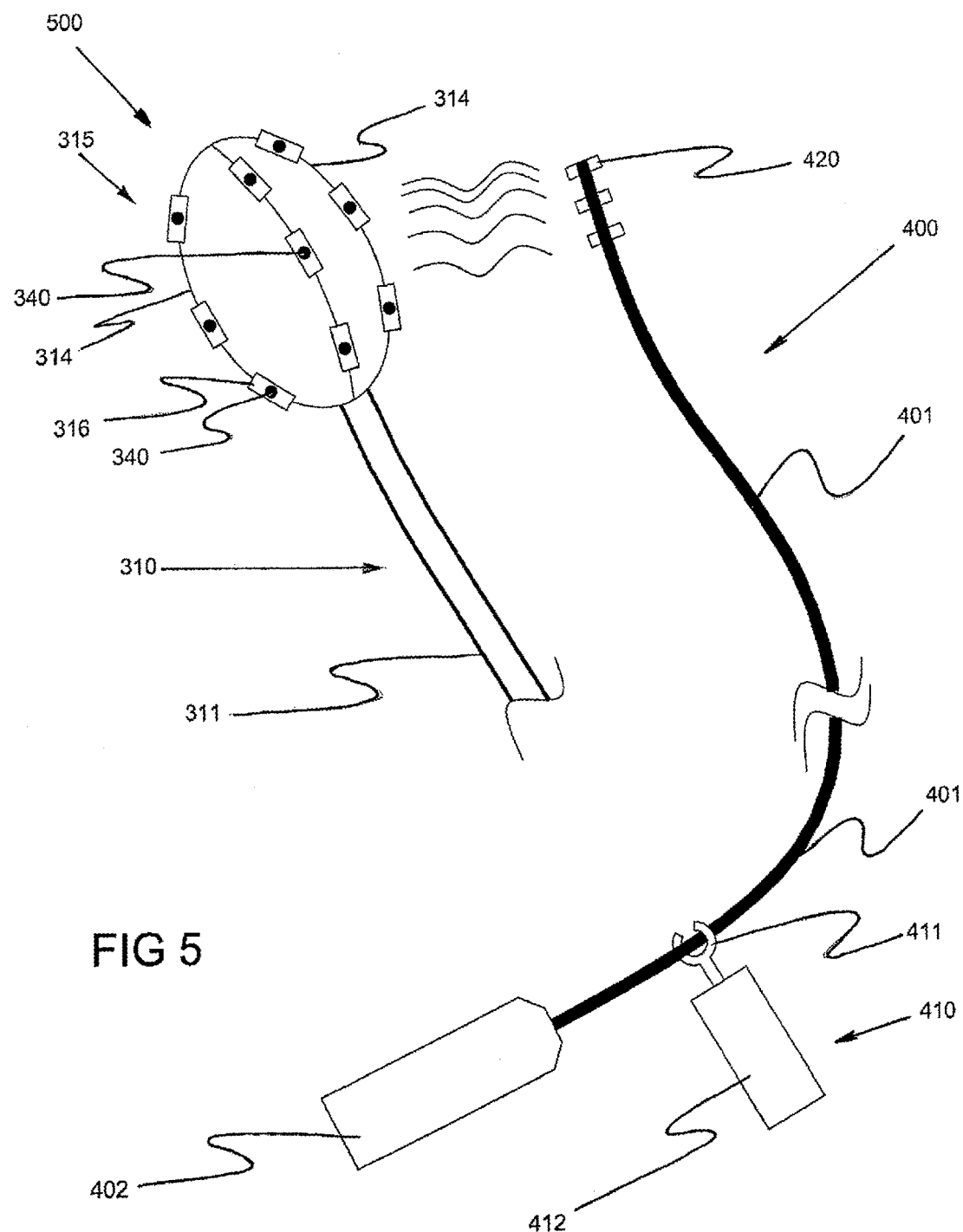
FIG. 5 illustrates a side view of a system including a mapping catheter comprising multiple sensors, an ablation catheter comprising multiple ablation elements and a clamping assembly attached to the ablation catheter, consistent with aspects of the present invention.

Ultrasound crystal 340 is configured to detect ultrasound waves, such as ultrasound waves produced by ultrasound emitter 341, preferably a removable clamping assembly including emitter 341 and clamped to shaft 311 of mapping catheter 310 as is described in detail in reference to FIG. 5 herebelow. Emitter 341 is configured to produce high frequency vibrations, i.e. ultrasound waves in a pulsed or constant manner. One or more sound emitting devices, such as devices configured to clamp to one or more catheters, may be used to transmit sound to one or more crystals 340. In one embodiment, a first clamping assembly with a particular ultrasound frequency may be used with a first catheter, while a second clamping assembly with a second ultrasound frequency may be used with a second catheter. In another embodiment, ultrasound sensor 340 is positioned on a second elongate shaft, not shown but configured to be inserted into mapping catheter 310, such as through one or more lumens, not shown, of mapping catheter 310. In a preferred embodiment, one or more crystals 340 may be configured to both record and transmit ultrasound waves, such as to avoid the need for emitter 341. Crystals 340 and electrodes 316 may be provided in various ratios, such as a ratio of two electrodes to one ultrasound crystal, such as when each ultrasound crystal 340 has an electrode 316 positioned at each end. In another embodiment, a ratio of five electrodes 316 to two crystals 340 is provided, such as a catheter shaft including sets of two assemblies with a single electrode 316 positioned in between. Each assembly includes an ultrasound crystal 340 with an electrode 316 positioned at each end.

In an alternate embodiment, a drive shaft 320 is operably connected to a rotation mechanism, not shown but configured to rotate shaft 320 causing one or more crystals 340 to rotate within electrode 316 or another portion of catheter 310. As described in reference to FIG. 1 hereabove, crystal 340 may rotate a full 360° or may rotate through an arc less than 360°. Alternatively, catheter 310 may comprise a plurality of crystals 340 arranged in an array, for example, a circumferential array surrounding shaft 311, one or more electrodes 316 and/or a support arm 314 of array 315, such as a phased array of crystals configured to produce a 360° ultrasound image, well known to those of skill in the art.

In another embodiment, ultrasound sensor 340 comprises a probe, not shown, but typically a probe removably attached to or inserted within catheter 310. In an alternate embodiment, ultrasound sensor 340 comprises a piezoelectric film, not shown but typically covering one or more electrodes 316 within array 315. In yet another embodiment, ultrasound sensor 340 comprises a piezoelectric cable, not shown but operably connected to one or more electrodes 316.

Referring now to FIG. 5, a side view of a system including a mapping catheter comprising a sensor and an ablation catheter comprising a transducer is illustrated. System 500 comprises mapping catheter 310 and ablation catheter 400.

Mapping catheter 310 comprises shaft 311 including array 315 on its distal end. Array 315 includes one or more electrodes 316 mounted to one or more arms 314, each electrode configured to record cellular activity in tissue. Array 315 further includes one or more ultrasound emitting crystals 340, each positioned between two electrodes 316. Crystals 340 may be configured to both record and transmit ultrasound waves.

Ablation catheter 400 comprises shaft 401, having a proximal portion with a proximal end and a distal portion with a distal end, and clamping assembly 410. Clamping assembly 410 is shown positioned on shaft 401 proximate handle 402, i.e. the proximal portion of shaft 401, such as at a location 10 cm from the proximal end of shaft 401. Clamping assembly 410 comprises ultrasound transducer 412 and clamping mechanism 411 configured to removably attach clamping assembly 410 to shaft 401 of catheter 400. Additionally, ablation catheter 400 comprises multiple ablation elements, electrodes 420, located on the distal end of shaft 401 and configured to deliver ablation energy (e.g. RF energy) and also to receive the ultrasound vibrations produced by clamping assembly 410 and ultrasound transducer 412. In turn, electrodes 420, and one or more other components of ablation catheter 400, emit ultrasounds waves. The emitted ultrasound waves are received by ultrasound crystals 340 of catheter 310, and can be used to produce position information relative to one or more components of ablation catheter 400 and/or mapping catheter 310. Clamping assembly 410 is configured to produce high frequency vibrations, i.e. ultrasound waves in a pulsed or constant manner, typically with a frequency between 5 and 18 MHz. In another embodiment, ablation catheter 400 may include a conduit, not shown but typically a solid or hollow tube configured to transmit the ultrasound waves from the proximal portion to the distal portion of ablation catheter 400.

In an alternate embodiment, one or more support arms, not shown, may be attached to ablation catheter 400 (e.g. similar to the support arms 314 of array 315 of catheter 310), and electrodes 420 may be located on the one or more support arms. The support arms may be radially distributed about ablation catheter 400 and may comprise various geometric shapes, e.g. circular or rectangular. In this embodiment, clamping assembly 410 may be constructed and arranged to vibrate the one or more support arms, in turn vibrating the one or more electrodes, thus transmitting ultrasound waves to sensors 340. In another embodiment, electrodes 420 may be configured to record electrical activity in cells as well as deliver ablation energy.

In one embodiment, catheter 400 may further include one or more sensors, not shown but typically including one or more sensors selected from the group consisting of: a temperature sensor, such as a thermocouple; a pressure sensor; an acoustic sensor, such as an ultrasound crystal; an electromagnetic sensor, such as an electrode configured to record electrical information produced by living cells; and combinations of these. Clamping assembly 410 may be constructed to transmit vibrations to the one or more sensors such that ultrasound waves transmitted by the one or more sensors can be detected by crystals 340 of catheter 310 and/or another sensor of the system, such that geometric and other position information can be determined and utilized by a clinician to perform a medical procedure.

Alternatively or additionally, catheter 400 may further include one or more transducers, not shown but typically including one or more transducers selected from the group consisting of: an ablation element such as an energy delivering electrode, a cryogenic transducer, a microwave transducer and/or a laser delivery element; a sound transducer, such as an ultrasound crystal; a heating element; a cooling element; a drug delivery device; and combinations of these. Clamping assembly 410 may be constructed to transmit vibrations to the one or more transducers such that ultrasound waves transmitted by the one or more transducers can be detected by crystals 340 of catheter 310 and/or another sensor of the system, such that geometric and other position information can be determined and utilized by a clinician to perform a medical procedure.

Clamping assembly 410 may be attached to any ablation catheter, eliminating the need for a customized catheter. As discussed hereabove, clamping assembly 410 is constructed and arranged to vibrate one or more components of a catheter, such as a sensor or transducer of the catheter, such that one or more sensors, typically ultrasound sensors, can identify the location of the sensors or transducers vibrated by the clamping assembly. In one embodiment, a first clamping assembly with a particular ultrasound frequency may be used with a first ablation catheter, while a second clamping assembly with a second ultrasound frequency may be used with the same ablation catheter. Alternatively or additionally, electrodes 420 may include a piezo crystal or otherwise be configured to transmit ultrasound waves that can be received by crystals 340 of catheter 310.

Figure 6:
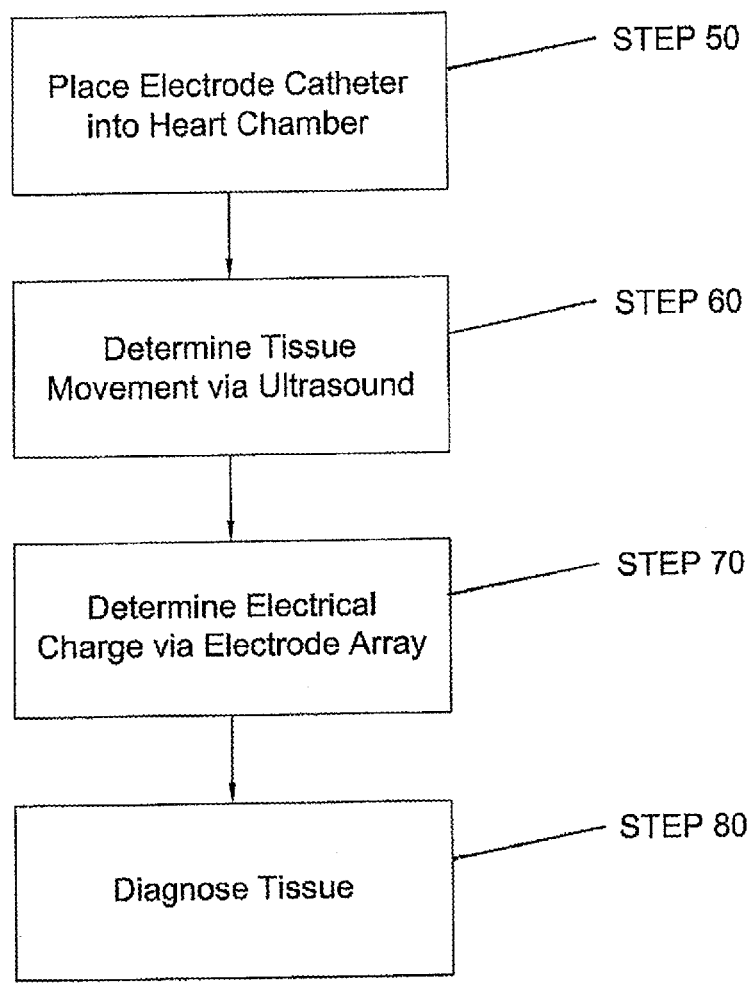
FIG. 6 illustrates a flow chart of an embodiment of a preferred method for diagnosing the tissue of a patient, consistent with aspects of the present invention.

Referring now to FIG. 6, a flow chart of an embodiment of a method for diagnosing the tissue of a patient is illustrated. In STEP 50, the distal end of an electrode catheter is placed into one or more body locations, such as one or more cardiac chambers of a patient. The electrode catheter comprises at least one electrode and at least one ultrasound element. The electrode catheter includes one or more electrodes positioned on a distal portion of the catheter and configured to record electrical activity in tissue and/or deliver ablation energy. In STEP 60, anatomical information, such as tissue location, tissue movement, tissue thickness and/or tissue contour information may be determined via the at least one ultrasound element, typically an element configured to transmit and receive ultrasound waves. Alternatively or additionally, position and/or distance information can be recorded, such as position and/or distance information relative to one or more device components and/or tissue locations. In STEP 70, the electrical charge of one or more tissue locations may be determined via the at least one electrode. STEPs 60 and 70 may be performed simultaneously or sequentially, in full or partial steps, and in any order. Either or both STEPs 60 and 70 may be performed in two or more independent time periods. In STEP 80, an analysis of the ultrasound reflections recorded and the electrical charge information is performed. This analysis includes producing a diagnosis and/or prognosis of the tissue portion. For example, electrical information indicative of adequate electrical activity and anatomical information indicative of the adequacy of tissue motion may correlate to presence of healthy tissue.

For example, electrical information indicative of adequate electrical activity and anatomical information indicative of adequate tissue motion correlates to presence of healthy tissue. Additionally, electrical information indicative of adequate electrical activity and anatomical information indicative of inadequate tissue motion correlates to presence of at least one of ischemic tissue or hibernating tissue. Conversely, electrical information indicative of inadequate electrical activity and anatomical information indicative of inadequate tissue motion correlates to presence of scar tissue. Additionally, electrical information indicative of inadequate electrical activity and anatomical information indicative of inadequate tissue motion correlates to presence of a complete ablation, such as an ablation performed in a cardiac ablation performed to treat a cardiac arrhythmia. In some embodiments, the complete ablation comprises a transmural ablation. In this use, the diagnosis and/or prognosis can include the confirmation of the creation of a transmural lesion in the patient's heart tissue, such as when both tissue motion and electrical activity have been eliminated or decreased below a threshold.

More specifically, the following four cases may exist:
Case 1: Electrical and anatomical are adequate—Tissue is healthy,
Case 2: Electrical is adequate and anatomical is inadequate—Tissue is compromised,
Case 3: Electrical is inadequate and anatomical is adequate—Tissue is compromised, and
Case 4: Electrical and anatomical are both inadequate—Tissue necrosis.

The actual threshold for determining adequacy of electrical function of any one area of the heart is dependent upon many factors, including the degree of coordination of the activation pattern and the mass of the cells being activated. Additionally, this threshold will be different for each chamber of the heart as well as from smaller to larger patients. For example, a threshold of 0.5 mV may be appropriate, wherein an electrical potential smaller that 0.5 mV may be indicative of inadequate electrical function and an electrical potential at or larger than 0.5 mV may be indicative of adequate electrical function.

Also included in the tissue diagnostic, a clinician may assess the electrical integrity of cardiac cells. For example, the functional status of the cardiac cells may be assessed. In one embodiment, the electrical information comprises dipole density information. Additionally or alternatively, the electrical information may comprise at least one of repolarization or speed of repolarization information.

The method may further comprise ablating the cardiac tissue based upon the tissue diagnosis. For example, the anatomical information comprising tissue thickness information and at least one of the magnitude of ablation energy or the time period in which ablation energy is delivered, is adjusted based on the tissue thickness information recorded by one or more ultrasound sensors.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

We claim:

1. A method of displaying cardiac information, said method including:
   providing an assembly comprising a plurality of electrodes, at least one ultrasound transducer, and at least one ultrasound sensor;
   using the plurality of electrodes, recording measured potentials V(x) from one or more cardiac chambers;
   emitting soundwaves from the at least one ultrasound transducer in a direction of the one or more cardiac chambers and receiving soundwave reflections by the at least one ultrasound sensor;
   producing by a distance measurement unit a set of data representing a distance between each transducer and a surface of tissue of the one or more cardiac chambers from the received soundwave reflections; and
   displaying at a display cardiac information based on the measured potentials V(x) from the one or more cardiac chambers and the set of data representing the distance between each transducer and the surface of the tissue of the one or more cardiac chambers.

2. The method of claim 1, wherein displaying cardiac information comprises displaying voltage potentials based on the measured potentials V(x) in association with the one or more cardiac chambers.

3. The method of claim 1, wherein displaying cardiac information comprises producing continuous images.

4. The method of claim 1, wherein displaying cardiac information comprises displaying continuous, real-time information related to electrical activity associated with tissue of the one or more cardiac chambers.

5. The method of claim 1, wherein displaying cardiac information comprises producing at least one real-time image.

6. The method of claim 1, wherein displaying cardiac information comprises producing images of the tissue of the one or more cardiac chambers.

7. The method of claim 6, wherein the images comprise at least one image of the one or more cardiac chambers.

8. The method of claim 6, wherein the images further comprise at least one image of at least one of the multiple electrodes.

9. The method of claim 1, further comprising:
   providing by the assembly motion information of the tissue of the one or more cardiac chambers to at least one of a display or an analyzer.

10. The method of claim 1, further comprising providing by the assembly thickness information of the tissue of the one or more cardiac chambers to at least one of a display or an analyzer.

11. The method of claim 1, further comprising:
   producing by the distance measurement unit a distance measurement comprising a distance between at least one of the multiple electrodes and a wall of a cardiac chamber.

12. The method of claim 1, further comprising:
   providing by a processing device tissue diagnostic information in response to the processing device analyzing both tissue motion information and cell electrical signals.

13. The method of claim 12, further comprising:
   providing the tissue diagnostic information during a cardiac ablation procedure.

14. The method of claim 1, further comprising:
   providing by the assembly a location of cardiac tissue with electrograms.

15. The method of claim 1, wherein the at least one ultrasound transducer and the at least one ultrasound sensor comprise at least one transducer and sensor in a single component.

16. The method of claim 15, wherein the single component comprises a single ultrasound crystal.

17. The method of claim 1, wherein the at least one ultrasound sensor and/or the at least one ultrasound transducer comprises an array of components.

18. The method of claim 17, wherein the array comprises an array of ultrasound crystals.

19. The method of claim 1, wherein one or more of the at least one ultrasound transducer produces signals with a frequency between 3 Mhz and 18 Mhz.

20. The method of claim 1, wherein the sensor comprises multiple sensors.

21. The method of claim 1, wherein the array comprises a multiple arm assembly that includes a plurality of electrodes and a plurality of ultrasound transducer-sensor pairs mounted thereon.

22. The method of claim 1, further comprising:
providing a dipole density module configured to determine dipole densities d(y) based, at least in part, on the measured potentials V(x).

23. The method of claim 22, wherein the displayed cardiac information comprises the dipole densities d(y).

24. The method of claim 22, wherein the displayed cardiac information comprises the dipole densities d(y) and voltage potential measurements based on the measured potentials V(x) within the one or more cardiac chambers.

25. The method of claim 22, further comprising:
providing a first receiver constructed and arranged to receive mapping information from the plurality of electrodes, the mapping information received when the plurality of electrodes are placed in the one or more cardiac chambers;
wherein the dipole density module is constructed and arranged to generate a three dimensional database of dipole densities d(y), wherein the dipole density module determines a dipole density for individual triangle shaped projections onto a cardiac chamber wall, where each triangle projection at a location y contributes ω(x,y) times the dipole density d(y) to a potential V(x) at a point x, wherein (ω)(x,y) is the solid angle for that triangle projection, and where:
a) x represents a series of locations within one or more cardiac chambers; and
b) V(x) is a measured potential at point x, said measured potential recorded by the multiple electrodes.

26. The method of claim 25, further comprising:
determining a dipole density for at least 1000 triangle shaped projections.

27. The method of claim 25, further comprising:
interpolating the measured potentials V(x) to increase a number of regions of the cardiac chamber wall, each region comprising at least one triangle projection.

28. The method of claim 25, further comprising:
providing a second receiver configured to receive additional mapping information from one or more skin electrodes.

29. The method of claim 28, further comprising:
the dipole density module using said additional mapping information to generate the three-dimensional database of dipole densities d(y).

30. The method of claim 22, further comprising:
the dipole density module determining a map of dipole densities d(y) at corresponding time interval.

31. The method of claim 22, further comprising:
the dipole density module generating a synthesis of maps that represents a cascade of activation sequences of each corresponding heart beat from a series of heart beats.

* * * * *